United States Patent [19]

Bahler

[11] Patent Number: 5,395,401
[45] Date of Patent: Mar. 7, 1995

[54] PROSTHETIC DEVICE FOR A COMPLEX JOINT

[76] Inventor: André Bahler, Kapfsteig 44, CH-8032 Zurich, Switzerland

[21] Appl. No.: 898,326

[22] Filed: Jun. 15, 1992

[30] Foreign Application Priority Data

| Jun. 17, 1991 | [CH] | Switzerland | 01795/91 |
| Jun. 17, 1991 | [CH] | Switzerland | 01796/91 |
| Dec. 19, 1991 | [CH] | Switzerland | 03783/91 |

[51] Int. Cl.⁶ .............................................. A61F 2/38
[52] U.S. Cl. ............................................... 623/20
[58] Field of Search ............................... 623/16, 18, 20

[56] References Cited

U.S. PATENT DOCUMENTS

| 4,085,466 | 4/1978 | Goodfellow et al. | 623/20 |
| 4,207,627 | 6/1980 | Cloutier | 623/20 |
| 4,301,553 | 11/1981 | Nodes | 623/20 |
| 4,309,778 | 1/1982 | Buechel et al. | 623/20 |
| 4,340,978 | 7/1982 | Buechal et al. | 623/20 |
| 4,353,136 | 10/1982 | Polyzoides et al. | 623/20 |
| 4,470,158 | 9/1984 | Pappas et al. | 623/20 |
| 4,728,332 | 3/1988 | Albocktsson | 623/20 |
| 4,950,297 | 8/1990 | Elloy et al. | 623/20 |
| 5,007,933 | 4/1991 | Sidebotham et al. | 623/20 |
| 5,011,496 | 4/1991 | Forte et al. | 623/20 |

FOREIGN PATENT DOCUMENTS

| 9008190 | 12/1991 | France . |
| 3529894 | 3/1987 | Germany | 623/20 |
| 9110504.8 | 12/1991 | Germany . |
| 2061730 | 5/1981 | United Kingdom . |
| 2223950 | 4/1990 | United Kingdom . |
| WO89/06947 | 8/1989 | WIPO . |
| WO92/08424 | 5/1992 | WIPO . |

OTHER PUBLICATIONS

"New Jersey Tricompartmental Total Knee System".
"A Manuel of the Oxford Knee", published by OEC Orthopaedic Ltd. Bridgend, South Glamorgan, United Kingdom.

Primary Examiner—David Isabella
Attorney, Agent, or Firm—Frishauf, Holtz, Goodman & Woodward

[57] ABSTRACT

A first prosthetic part (11) is adapted to be attached to a femur; a second prosthetic part (17) is adapted for attachment to the tibia. An intermediate joint assembly has a meniscal part (13) and a coupling part (15) which is rotatable about an axis of rotation (39). The femoral part and an element of the intermediate joint assembly, respectively, have rotary joint surfaces (19, 21) which are essentially congruent. To permit the intermediate joint assembly to move in translatory direction in addition to rotation thereof about the axis (39), the assembly includes a guide portion (16) engaging a guide track (35), preferably formed on the meniscal and coupling parts, respectively. The guide track and the guide portion are interlocked, for example by forming the guide track and the guide portion in dovetail, tongue-and-groove connection, or the like. The guide track and guide portions extend in a direction which is essentially an analog of the physiological direction of sliding movement of a natural knee joint, which is being replaced by the prosthetic joint. To provide for increased stability, the guide portion may be formed with a stabilizing section (2136) which fits into a box-like stabilizing structure (2114) formed on the first prosthetic part (2111). It is possible to provide modular sets of prosthetic joint parts to meet various requirements.

43 Claims, 19 Drawing Sheets

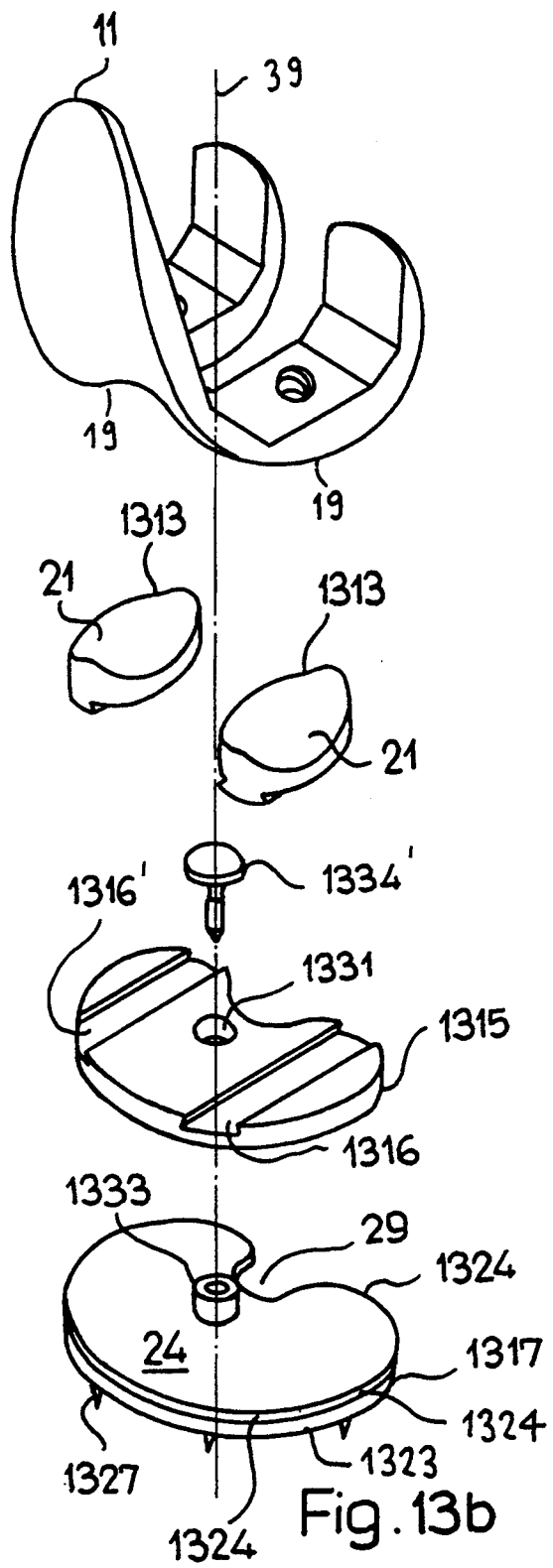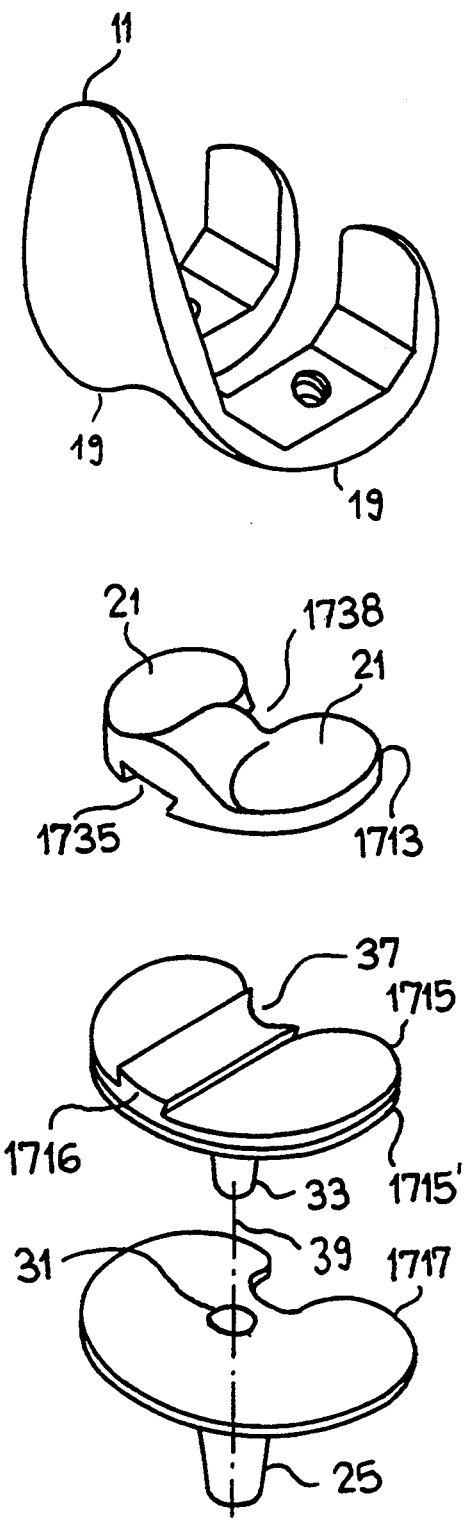

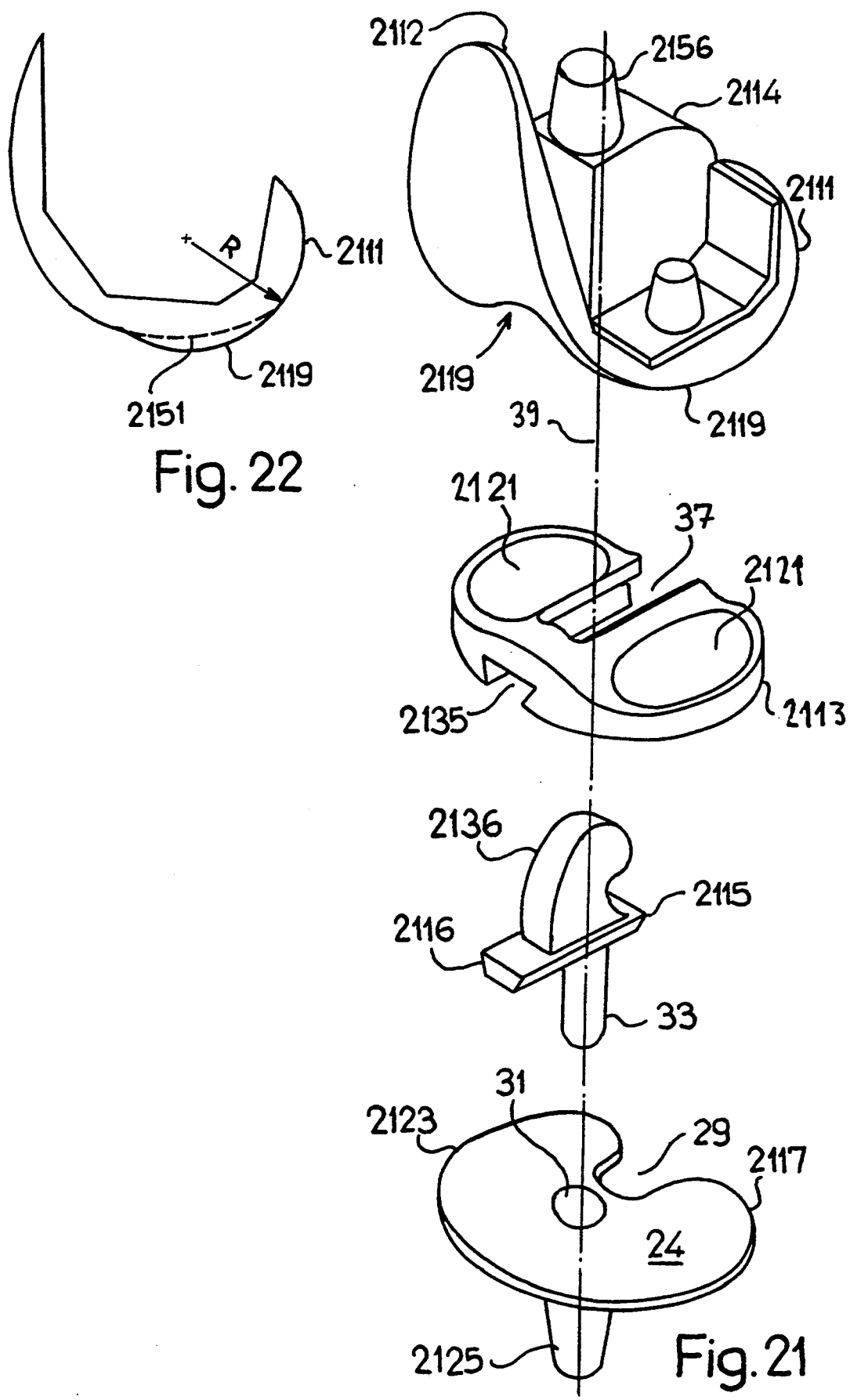

PROSTHETIC DEVICE FOR A COMPLEX JOINT

FIELD OF THE INVENTION

The present invention relates to a prosthetic device for a joint, and more particularly for a complex joint, and especially for the knee joint, having a first prosthetic part which contains an anchoring or attachment portion and at least one rotary joint portion, adapted to be secured to one of the bones which form the joint, for example the femur, and a second part which also contains attachment elements or stems, adapted to be attached to the shin bone or tibia, and formed with a sliding surface. An intermediate part or element is provided which is rotatable about an axis of rotation and furthermore is slidable. The intermediate portion is so shaped that, in association with a suitable section of the first portion, rotation can be effected.

BACKGROUND.

Many solutions have been proposed for the problem of endoprosthetics, which permit unchangeable maintenance of a stable bone implantate joint, which will last for a very long time, ideally from implantation to the death of the patient or wearer of the prosthesis. There are, primarily, two factors which interfere with such lifetime implantation. For one, the interface between the bone-implantate is subject to changeable forces, which change both with respect to value as-well as direction. Particularly shearing forces are involved. For another, biological reactions of tissues and degrading bones are a factor, especially reactions to foreign-body materials, and reactions to abraded particles from the prosthesis itself.

The long lifetime, and particularly implanted lifetime, of a joint can be increased by reducing changeable forces engaging at the interface between the various prosthetic parts, and on the sliding surfaces thereof. The wear on the sliding surfaces should be minimized. Various solutions have been proposed, but not all of them can be applied at the same time. It is not sufficient to consider all the technical aspects of the joint; anatomical as well as physiological changeable conditions must be considered. The complex kinematic which occurs in joints, and particularly in complex joints such as the knee joint, can make it difficult to compromise between conflicting solutions applicable to specific parts, to achieve the overall goal of lifetime reliability.

It is well known that the wear and tear on slide bearings can be reduced by decreasing the per-square or area pressure of the respectively rubbing sliding parts. The surface or area pressure, and the resulting wear and tear on the bearing, is small when the contact surface of the two sliding elements is large. This contact bearing surface can be increased by making the sliding surfaces as large as possible and effectively congruent. Typical examples for such bearings are shown in FIG. 1, in which a straight slide bearing is schematically illustrated, and in FIG. 2, which, schematically, illustrates a hinge or ball joint. The slide bearing of FIG. 1, in principle, can be considered as a hinge or ball joint in which the engaging surfaces have infinite radii. Yet, in spite of the common characteristic of minimal wear and tear, there are basic differences: The slide joint, FIG. 1, is free for translatory movement, but does not have an axis of rotation. The hinge or ball joint, on the other hand, has an axis of rotation, but is restrained from translatory movement. This results in different relationships with respect to externally acting forces.

Reference is again made to FIG. 1:

A force, such as force F1 coming from above at an inclination, results in lateral shifting of the sliding head due to horizontal component of the force. This horizontal component of the force does not have any effect on the lower part of the sliding joint.

A force similar to force F1, when applied to a hinge or ball joint, see FIG. 2, passes through the joint without causing any rotation thereof. The horizontal component of this force, however, results in an undesired shear force, which continuously changes its direction if the upper portion of the joint oscillates back and forth like a pendulum. Most simply, the hinge joint has the advantage of rotary movement, which, however, is obtained by accepting the disadvantage of translatory immobility, and shearing forces at the interface.

Human body joints rarely are pure hinge joints or pure slide joints. Usually, and especially the knee joint provides a combination of both. A rotary movement and translatory movement can be superimposed upon each other.

In order permit a combination of such movements, it is necessary to open the hinge joint, that is, it is necessary to reduce the congruence of the slide surfaces with respect to each other. Referring to FIG. 3, the contact surfaces are decreased which, however, substantially increases the area or surface pressure, and hence wear and tear on the joint. This wear and tear is further increased by repetitive translatory movement of the head of the joint on the slide surface. Due to the almost point or at best somewhat line contact, and hence a highly increased surface pressure, a kneading process on the respective joint parts results which, in turn, causes material fatigue of the lower joint portion or component. The non-congruent position of the elements does not necessarily prevent the occurrence of shear forces at the interface. Raised slide surfaces at the interface result in forces which are similar to those which arise in a pure hinge or ball joint. The result is increased wear and tear as well as shear forces at the interface, which has undesirable effects in all prostheses of this type.

It has been proposed to use a combination of slide and ball joints, in which the sliding and ball joint components are located on two different planes, by using an intermediate element, see FIG. 4. The rotary movement of the ball joint and a translatory movement of the slide joint are vertically staggered, so that the translatory movement is available as a lower motion of the ball joint. The congruence of joint surfaces is fully retained; wear and tear is minimized. The forces supplied by the ball joint are not transferred to the interface but, rather, translated into translatory movement by the intermediate element. Prostheses are of this type are known, and have been referred to as meniscal knees.

U.S. Pat. No. 4,309,778, Buechel and Pappas, describes two different knee joint prostheses, which have also been referred to as the "Oxford Knee" and the "New Jersey Knee". The "Oxford Knee" has two femoral portions, two intermediate portions and two tibial portions. The femoral portions each have a spherical segment which has a retention section, for retention on the femur. The tibial parts also have retention on the tibia. The tibial parts not only have retention sections for attachment to the tibia, but also a flat plateau on which the intermediate part can slide.

Upon flexion of 90° and more, the intermediate part can slide over the flat or table-like surface and, possibly, can be entirely dislocated. A similar danger may occur if the tension of the remaining ligaments decreases after the operation and the femoral part lifts off the intermediate part. A new operation of the knee joint will then become necessary.

The "New Jersey" described for example in FIG. 15 of the referenced U.S. Pat. No. 4,309,778, has a special arrangement to prevent loss of contact over the table or slide surface. Two dovetail-like, bowed grooves are provided on the tibia part; an engagement element is provided for the intermediate part element, fitting in the grooves through which the intermediate part element are constrained to be guided. The curves are directed towards the center, so that the intermediate part, upon bending of the knee, cannot slide backwardly in uncontrolled manner, and pushed over the surface or table, but, rather, engages the still remaining central projection from the bone. The dovetaile shape prevents dislocation or luxation of the joint, if the ligaments should lose tension or will have decreased tension or strength.

The intermediate portions are constrained to be guided on a predetermined path which permits congruence of the joint surfaces between the femoral portion and the intermediate portion only in a single position of the joint. For all other positions of the joint than the single one, an incongruence of joint surfaces results, which increases wear and tear of the engaging surfaces. Non-congruent conditions arise because the femoral parts, which are securely anchored in the femur, are always at the same distance from each other and have a common axis of rotation. The intermediate parts, however, approach each other laterally upon sliding forwardly and backwardly on the curved path or, respectively, separate from each other. Further, the axes of the hinge or ball joints continuously change their position with respect to each other. Similar situations obtain, in reverse sense, however, upon rotary movement about an axis which is perpendicular to the slide surface. The continuously changing degree of non-congruence of the surfaces of this prosthesis, and particularly of the hinge or ball joint surfaces, causes increased wear and tear and decreases the effect of a meniscal layer in a knee joint.

U.S. Pat. No. 4,470,158, to which European Patent Specification 0 018 364 B1, Pappas and Buechel, corresponds, describes a knee prosthesis, which also has been termed a "rotating platform-type prosthesis". It includes a femoral portion, a tibial portion and an intermediate or meniscal portion. The femoral portion has the usual posts or stems to lock the femoral portions against the femur and two condyles, defining condylar bearing surfaces. The tibial portion or part also has fixation elements, for example a fixation fin or the like, for attachment to the tibia, and a central bore or opening for reception of a rotation pin forming part of the intermediate or meniscal portion. The intermediate or meniscal portion is formed not only with the twist or rotation post, but also is formed with two concave slide bearings for reception of the-condyles of the femoral part.

The prosthesis of this disclosure has the advantage of congruence of the slide surfaces of the hinge joints, which decreases wear and tear, and, further, luxation or dislocation of the meniscal bearing element is prevented due to the presence of the rotation pin.

However, the presence of the rotation pin does not permit translatory movement of the femoral part relative to the tibial part, in contrast to the earlier described embodiments. The rotation pin only permits the possibility of rotation about the axis of the pin itself. This, then, is a classic hinge joint with the additional freedom of rotation about an axis perpendicular to the joint. Inclined forces, such as the force F1, which arise, for example, by forces due to muscles, loading due to weight of the wearer upon placing the foot on a surface, or the like, will pass through the joint to the interface and there result in the undesired shearing forces. The principle of a meniscus knee again is compromised since the congruence of the joint surfaces, which reduces wear and tear, is obtained only by loss of the translatory possibility and the consequent natural kinematics of the knee which, otherwise, would protect and enhance the secure attachment of the prosthesis with the bones of the wearer.

In case of missing ligaments, or ligaments which no longer can assure the required stability, the prostheses of the referenced U.S. Pat. Nos. 4,309,778, Buechel and Pappas, as well as 4,470,158, Pappas and Buechel, have problems with stability. To ensure stability in medial as well as lateral and posterior direction, a knee joint prosthesis has been proposed (see British Patent 2,223,950, to which Published Application WO 90/04369—PCT corresponds), in which a femoral part, a tibial part and an intermediate or meniscal part are provided, and in which the meniscal part is pivotably retained. The meniscal part is formed with a finger which engages in a box structure of the femoral part. This box structure is so dimensioned that the finger is guided on at least three sides in any flexural position of the joint. Thus, stability is ensured in medial, lateral and posterior direction.

The structure of U.S. Pat. No. 5,007,933, Sidebotham et al (to which European Publication 0 381 352 A1 corresponds), also ensures lateral, medial and posterior stability. The prosthesis there described does not, however, have a pivotable meniscal or intermediate part. Translatory movement is not possible with the structure of either the British Patent 2,223,950., or the U.S. Pat. No. 5,007,933. Yet, this translatory possibility is required to protect, preserve and conserve the fixation or attachment of the prosthetic elements to the femur and tibia, respectively.

THE INVENTION

It is an object to provide a prosthesis for replacement of injured or diseased joints, and particularly complex joints, and especially of knee joints, which protects its components, when in use, has low wear and tear, and which permits rotary movement similar to that of a natural knee, with high assurance against dislocation, so that at least an approximately normal physiological movement of the wearer is possible. It is a specific object to provide a prosthesis which permits not only congruence of joint surfaces but translatory motion as well. All this should be possible even if ligaments are impaired or may even be missing, while still assuring stability to the wearer.

Briefly, the joint in accordance with the present invention has four parts, namely a first prosthesis part, a first intermediate part, a second intermediate part, and a second prosthesis part. The first and second intermediate parts form an intermediate joint means or assembly, or section. For a knee joint, they are a first prosthetic, femoral part; a meniscal part; a coupling part; and a second prosthetic, tibial part. In accordance with a feature of the invention, the elements of the intermediate assembly or section, e.g. the meniscal part and the coupling part, have a guide arrangement which is rotatable about an axis of rotation, e.g. a pin, and a guide track, which guide track extends at least approximately in the sliding direction of a true joint which is to be replaced, typically the knee, so that the meniscal joint, additionally to the twisting or pivoting or rotary movement, may also have translatory movement.

In accordance with a feature of the invention, the guide track is located within the intermediate assembly, preferably on the meniscal part.

In accordance with a feature of the invention, the pin defining the axis may be formed either on the coupling part, or the second prosthesis or tibial part, which results in a particularly simple construction.

In accordance with another feature of the invention, the coupling part may additionally be shaped in form of a stabilizing element which cooperates with a stabilizing structure of the first prosthesis part so that, even if the ligamentary system is weak, or missing, the stability is ensured, while permitting rotation.

The prosthesis according to the present invention permits movement which essentially is the same as the normal physical movement of a joint, especially of the knee joint. The first prosthesis part, as has been proposed before, is formed with condyles which, upon flexion, shift from ventral to dorsal region. At the same time, additionally, rotation may occur. In flexion as well as extension, the conditions are similar as in a natural knee. In any joint position, congruence of rotary or ball or hinge joint surfaces is ensured between the femoral part and the first intermediate or meniscal part. The joint surfaces on the first intermediate part can be fixed with respect to each other, but may be movable. Forces which are directed downwardly at any angle do not affect the interface in full intensity but, rather, are converted into translatory movement in the first intermediate or meniscal part. The danger of dislocation upon flexion, always so feared in prior art prostheses, is eliminated by the guide track.

In accordance with a feature of the invention, the rotation pin is located on the second intermediate or coupling part and rotatable in the second prosthetic part, typically the tibial part, to be rotatable with respect thereto. This results in a particularly simple construction. The rotation pin can be retained or journalled in a bore which extends into an attachment post. The pin can be comparatively long so that there will be no danger, after placing the prosthesis in the bone structure of the user, that it can lift out of its bearing bore. Special arrangements for axial holding of the rotation pin, thus, are not required.

In accordance with another feature of the invention, and forming another embodiment thereof, the rotation pin can be located on the second prosthetic part, typically the tibial part. The coupling part is rotatable on the pin. This construction has some advantages for some uses in that it is not necessary to form a large central hole or recess in the bone to receive the surrounding bearing and holding structure for the pin. Thus, the attachment posts on the second prosthesis part can be shaped and designed without considering the bearing pin and its holding sleeve or bearing tube. For example, the attachment posts or fins can be placed in peripheral position.

In accordance with a feature of the invention, the guide track is so arranged that, at least approximately, it follows physiological sliding movement. In a knee joint, the guide track can be arranged in approximately sagittal direction.

In accordance with a preferred feature, the guide track is curved, with a medial radius of curvature. The construction is preferably so arranged that the movability of the first intermediate or meniscal part relative to the guide portion of the coupling part is limited to moving in the plane of the slide path. Loss of control of the guide element in the guide track can readily be avoided by shaping the guide track and the guide element to have interengaging projection-and-recess sides, for example by forming the guide track and the guide element to have dovetailed, T-shaped, polygonal, tongue and groove, or other cross section. Thus, if the tension of ligaments should decrease after the operation, the elements will not separate from each other. In accordance with a preferred feature, the guide track is located preferably in the center of the first intermediate or meniscal part.

Various shapes are possible for the rotary portions of the joint in order to ensure rotary movement. In accordance with a preferred form of the invention, the rotary portion of the prosthesis joint is formed by two condyles in the first prosthesis part, which are associated with suitably fitting, congruent bearing surfaces on the first intermediate or meniscal part, so that the bearing surfaces and the condylar surfaces of the first prosthesis part are in matched association. The result will be a prosthesis which is very close to the natural joint of a knee.

In accordance with another embodiment of the invention, which is particularly suitable for a mono-compartmental joint, the rotary portions of the first prosthesis part are formed only by a single condyle. The result will be a prosthesis in which the single condyle cooperates with a single matching surface on the first intermediate or meniscal part, cooperating with that single condyle.

In accordance with another and desirable embodiment, the rotary portion of the first prosthetic part, e.g. the femoral part, is cylindrically curved. This results in a simple construction of the femoral part and a correspondingly formed meniscal part. If desired, and close to the natural model of a knee, the rotary portion may be formed with spherically bowed or curved surfaces similar to natural condyles. It is also possible, however, to form the rotary joint portion of the femoral part in spherically curved form and covering both natural condyles in a single element.

Preferable, the respective condyle or condyles are convex and the associated surface of the first intermediate or meniscal portion are concave. This is similar to the natural knee joint. It is also possible, however, and this may be desired in instances in which the anatomical structure so suggests, as, for example the patella-femoral joint, to reverse the arrangement and form the projections or condyles on the first intermediate element in convex form, and arrange the matching bearing surfaces as concave bearing surfaces in the first prosthesis part, in a knee joint typically the anterior femoral part.

The bearing surfaces themselves may be formed as replaceable or separately insertable elements fitted into a suitable recess of the first intermediate or meniscal part. This permits insertion of bearing elements of different height or thickness during the actual knee joint replacement operation. The change in the thickness may be necessary in order to compensate for insufficient elasticity or stretch of the ligaments, or for misalignments of skeletal axes. The intermediate portion in the bearing elements can be made of different materials, for example the intermediate element may be of metal and the bearing elements of a plastic material.

Use of replaceable or individually insertable bearing elements permits varieties of constructions, for example to form a recess in the first intermediate or meniscal part which is a shallow depression or is a through-opening. When the opening is a through-hole, the bearing element will engage on the slide surface of the second prosthesis part, in the knee joint typically the tibial part. This may have some advantage, particularly when the bearing element is made of a material which has excellent sliding characteristics with respect to the material of the slide surface. Preferably, the intermediate element is held at some distance or space from the slide surface, for example by the guide element of the coupling part.

When forming the prosthesis as a knee joint prosthesis, it is of advantage that the second prosthesis or tibial part, and the first intermediate part are formed with dorsal recess for the dorsal cruciate ligament. The prosthesis structure in accordance with the present invention readily permits the formation of such recesses. This arrangement has the advantage that the function of the dorsal cruciate ligament so important for suitable movement characteristics of the knee joint, is retained.

The rotary portions of the joint can also be so constructed that the condyles on the first prosthesis part have, each, an individual meniscal part with a bearing surface for each condyle, separately. Thus, the bearing elements for the respective condyles are associated with individual or a common meniscal part, each one of which may have its own guide track or which can operate along a single common guide track.

Shaping the coupling part with a stabilization portion, or a stabilization projection, cooperating with a similar stabilization structure in the first prosthesis or femoral part, ensures stability also if the ligaments are weak, or partly missing. Cooperation of the stabilization element with the stabilization structure also prevents bowleggedhess or knock-knee positions, while reliably preventing dislocation of the meniscal part upon flexion, even if the ligament structure is weakened.

The first prosthetic part can be a single-part element. To provide modular knee replacement structures or sets, it is suitable to form it in two parts, however, having a basic portion on which the stabilization structure can be attached as a separate element, used only when required.

The structure permits formation of a prosthesis for a knee joint for these conditions:
1) The posterior cruciate ligament and the lateral ligaments are present and are retained;
2) only the lateral ligaments are retained; and
3) neither the posterior cruciate ligament nor the lateral ligaments are retained.

The set may then contain at least two femoral parts, at least two second intermediate or coupling parts, at least one tibial part, and at least one meniscal or first intermediate part. The tibial part and the meniscal part are used in all the three above-listed cases 1), 2), 3). The femoral part and the coupling parts, however, differ. In case 1), the stabilizing elements need not be used. In the two cases 2) and 3), the stabilizing elements may differ from each other. It is also possible to apply additional accessories on the tibial part and the meniscal part. The general shape and dimension of the rotary portion of the joint from the femoral part to the meniscal part remain basically unchanged. Likewise, the rotary arrangement, its retention in the coupling part and the tibial part, as well as the guide elements and the guide track and the meniscal part, however, may remain unchanged, thereby ensuring compatibility of all components with respect to each other.

Providing the various parts of the joints, and specific guide elements and/or stabilization parts, in a construction or modular or set form has the advantage that the surgeon, with the same technique of operation, and without change of instruments, may construct the knee joint prosthesis, and assemble it during the operation. The tibial portion may be retained, if a subsequent operation should be necessary, to carry out conversion or, for example, if during the operation it turns out that the knee requires additional stabilization beyond that originally envisioned.

The knee joint set may contain single-element femoral parts, or it may contain base femoral parts, on which stabilization structures can be fitted to form a composite femoral part.

The femoral part, the meniscal or first intermediate part and the tibial part, each or any one of them, can be provided in different sizes, which can all be used with the same second intermediate or coupling parts.

DRAWINGS:

FIG. 13b illustrates the joint of FIG. 13a in exploded view;

FIG. 17b illustrates the joint of FIG. 17a in exploded view; FIG. 18 is a top view of the embodiment of FIG. 17a;

FIG. 21 is an exploded view of a knee joint prosthesis using a coupling element with a stabilization projection;

FIG. 22 is an illustration of a monocentric structure of a joint surface of the femoral portion;

Figures 28A, 28B, 28C:
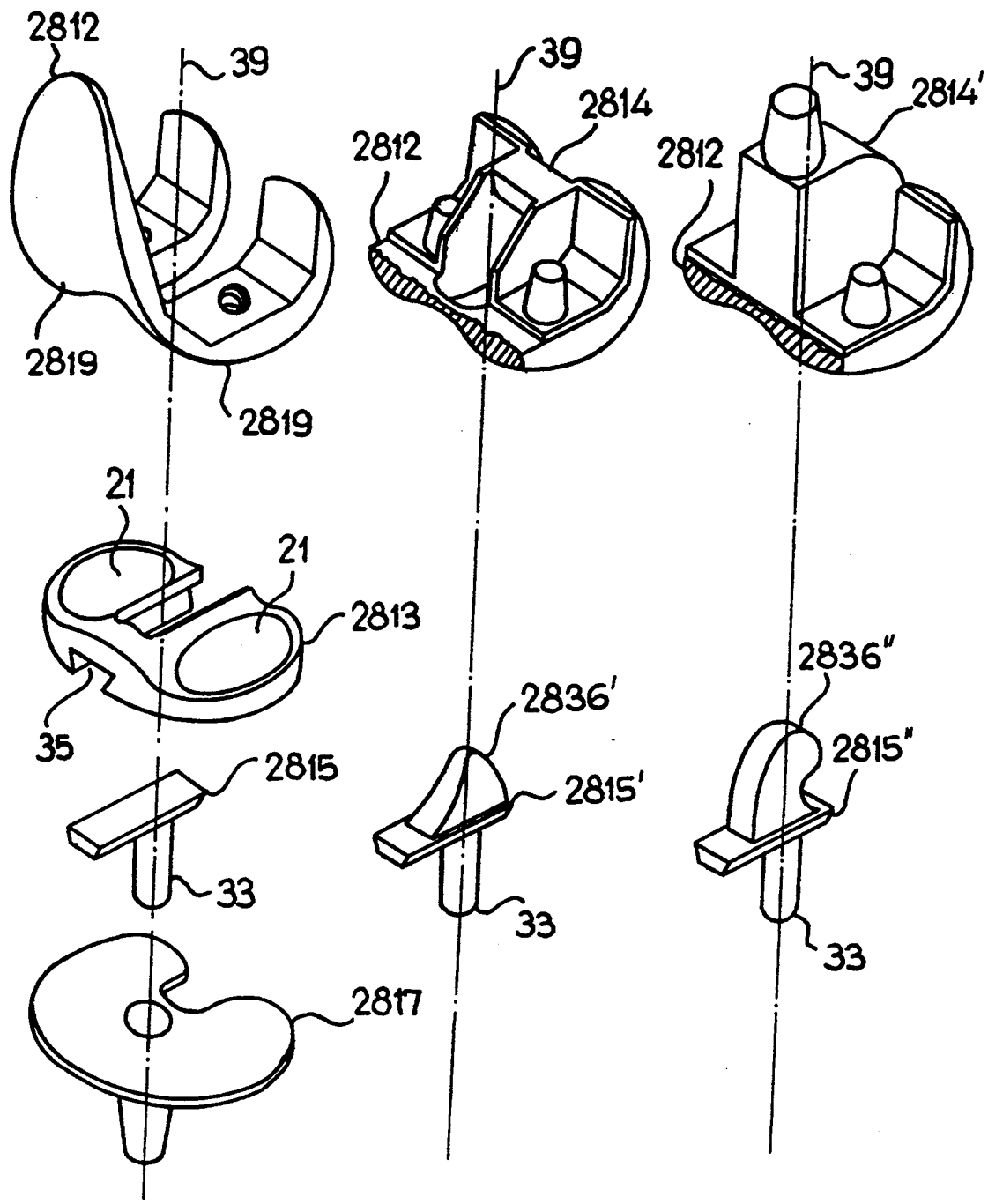

FIGS. 28a, 28b and 28c, in exploded view, illustrate different sets which, in dependence on the stabilization part, permit different constructions of the knee joint prosthesis, in which:

FIG. 28a is one suitable in which the posterior cruciate ligament and the lateral ligaments are retained;

FIG. 28b, wherein only the lateral ligaments are retained; and

Figure 29A:
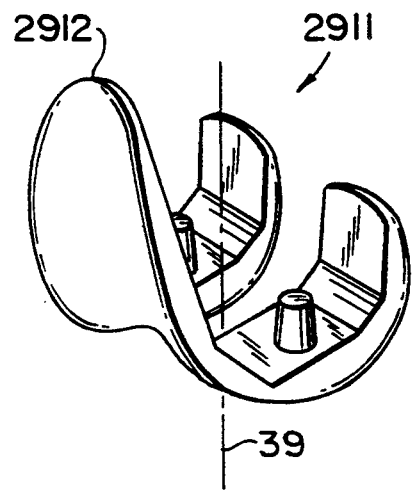
Figure 29B:
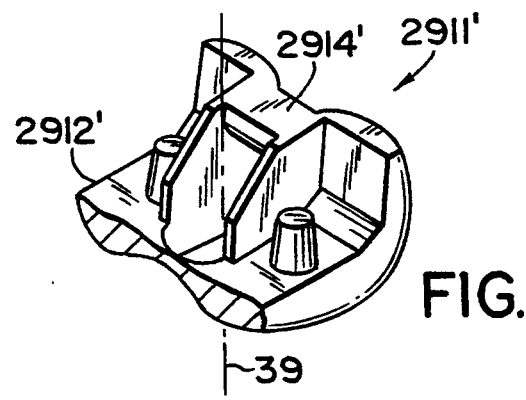
Figure 29C:
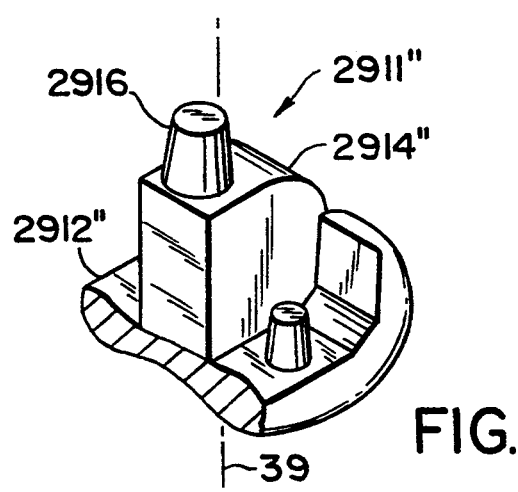
Figure 30:
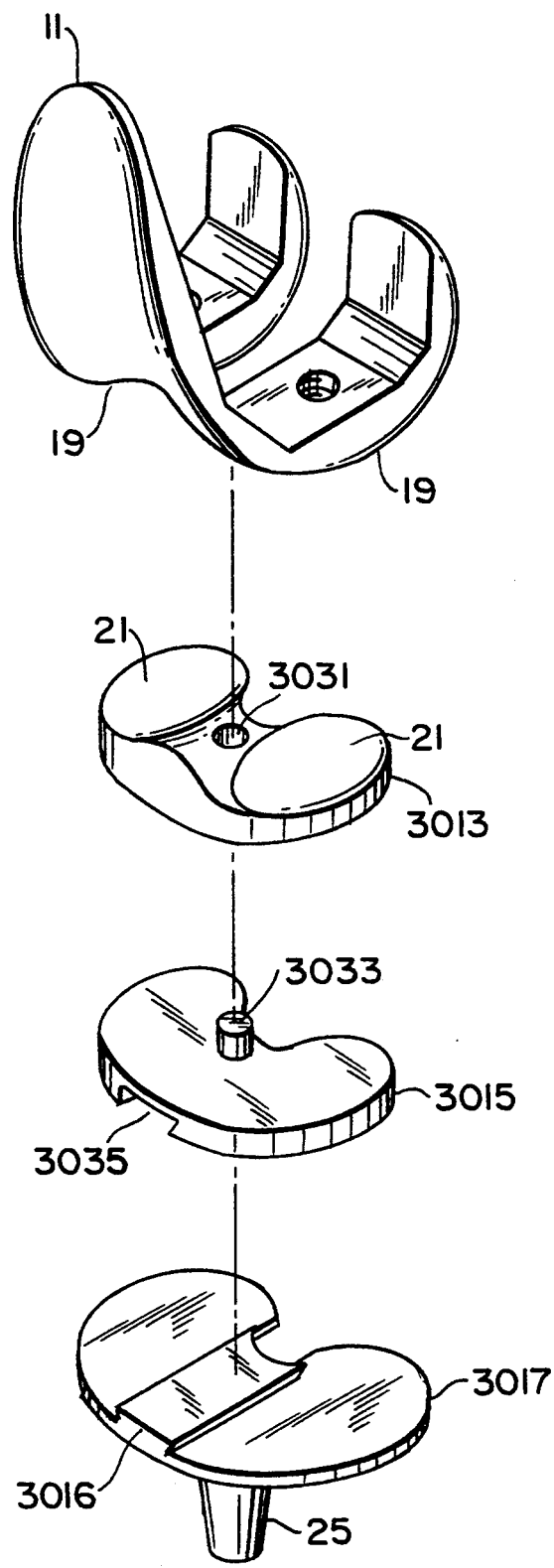

FIG. 28c in which neither the posterior cruciate ligament nor the lateral ligaments are retained;

FIGS. 29a, 29b, 29c illustrate a single-element or unitary femoral parts for use in the sets of FIGS. 28a, 28b, 28c, respectively; and FIG. 30 is an exploded view of a joint, similar to FIG. 17b, illustrating, however, another embodiment.

DETAILED DESCRIPTION

Figure 1:
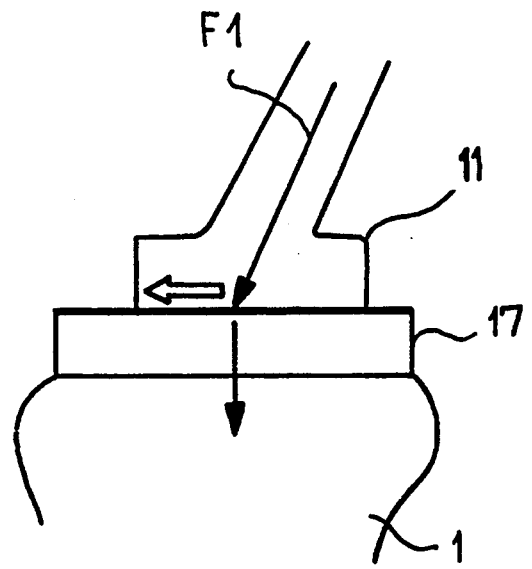
FIG. 1 is a highly schematic diagram illustrating force relationships in a sliding joint, and causing translatory movement.
Figure 2:
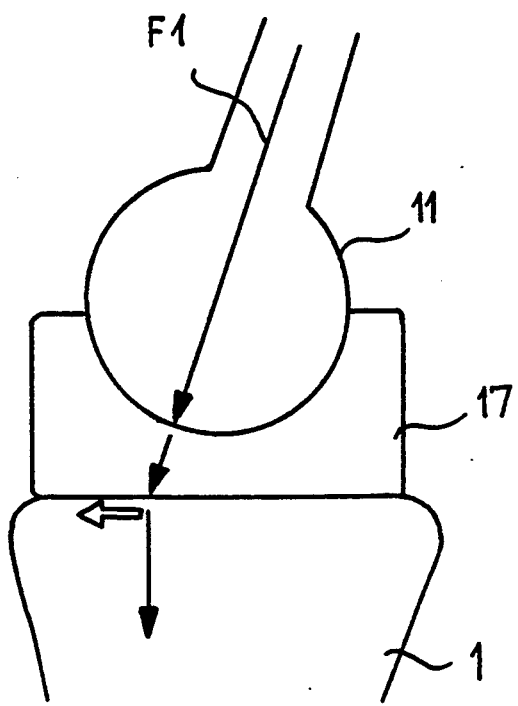
FIG. 2 is a highly schematic diagram showing shear forces which arise in a ball joint.
Figure 3:
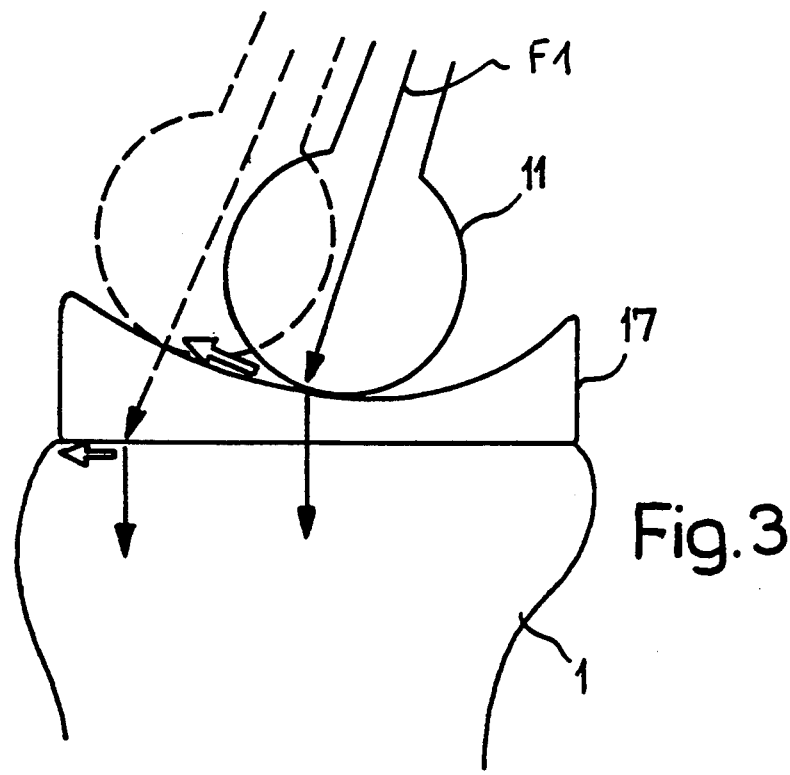
FIG. 3 is a highly schematic diagram illustrating forces which arise in an "open" ball joint.
Figure 4:
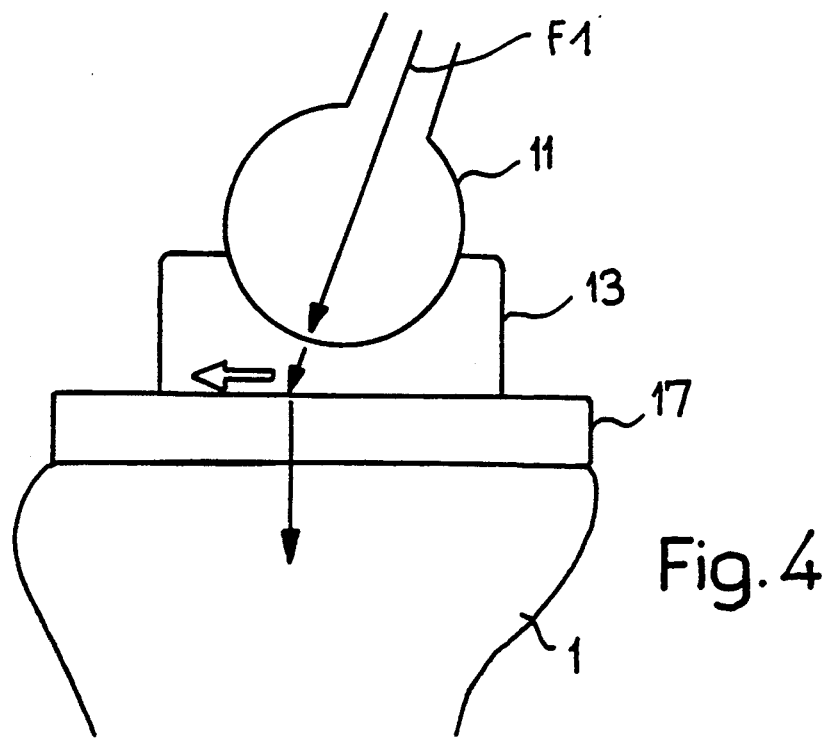
FIG. 4 illustrates the force relationships in a composite slide-ball joint.

FIGS. 1–4 show, highly schematically, the force relationships and force transfer conditions when a force F1 is applied by, for example, the femur or a femoral part 11 to a tibial part 17, secured for example to the tibia 1. FIG. 4 in addition shows the intermediate or meniscal element 13. In the actual joint, the element 11 is secured to the femur, not shown.

Figure 5:
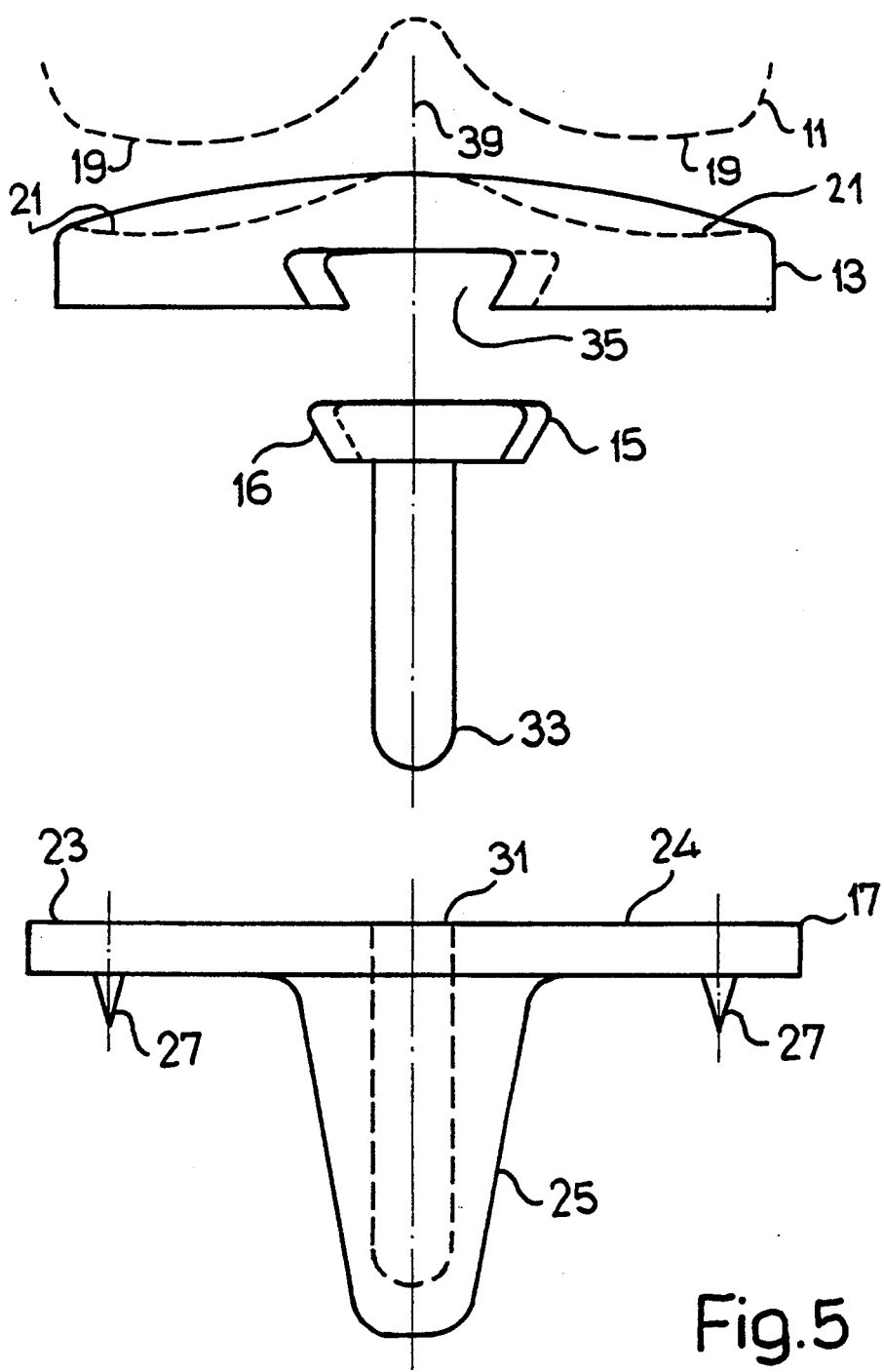
FIG. 5 is a schematic exploded side view of a combined slide and ball joint, to simulate a knee joint, in accordance with an embodiment of the invention.
Figure 9A:
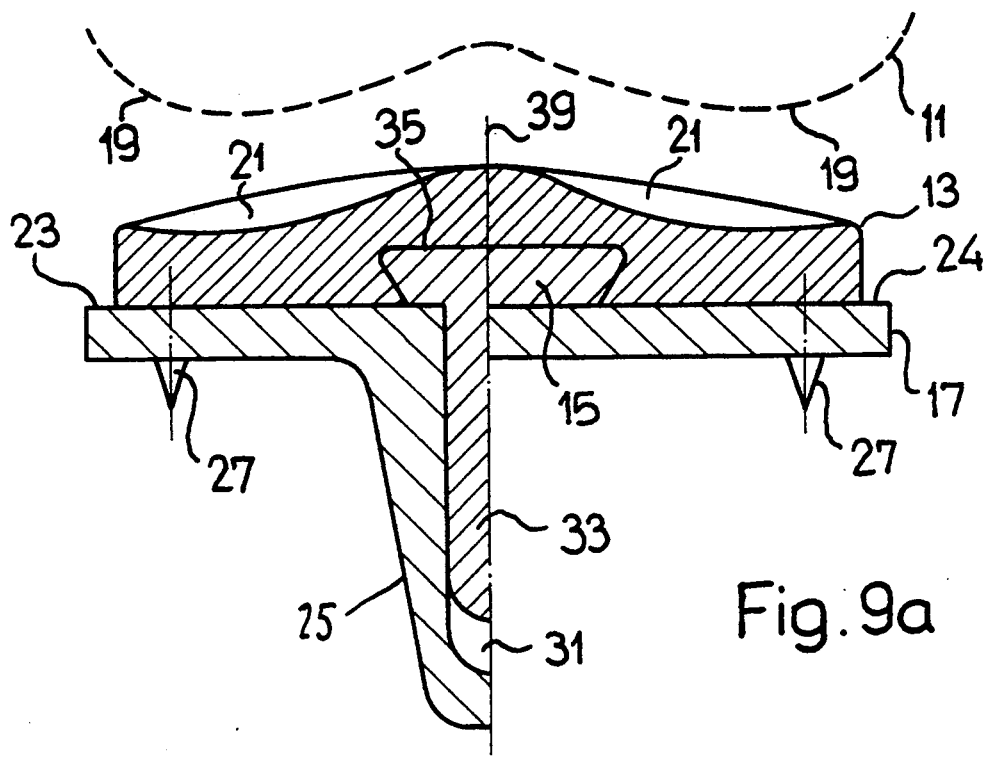
FIG. 9a is a cross section along the broken section line IX—IX in FIG. 8.
Figure 9B:
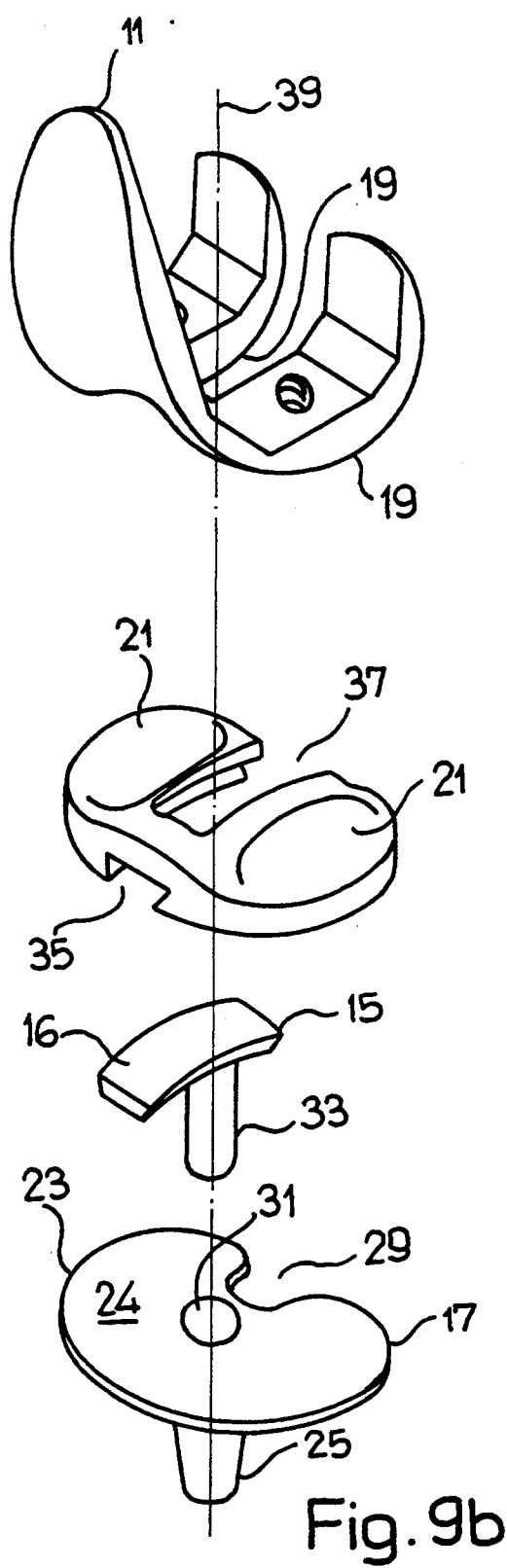
FIG. 9b illustrates the joint of FIG. 9a in exploded view.

According to the invention, and as best seen in FIGS. 5 and 9b, a coupling part 15 is provided. Thus, the overall prosthesis is formed by first or femoral prosthesis part 11, an intermediate or meniscal part 13, a second intermediate or coupling part 15 and a second prosthesis 17, adapted to be attached to the tibia, substantially in the direction of the axis of the tibia, as shown, only schematically, in FIG. 4.

Figure 7:
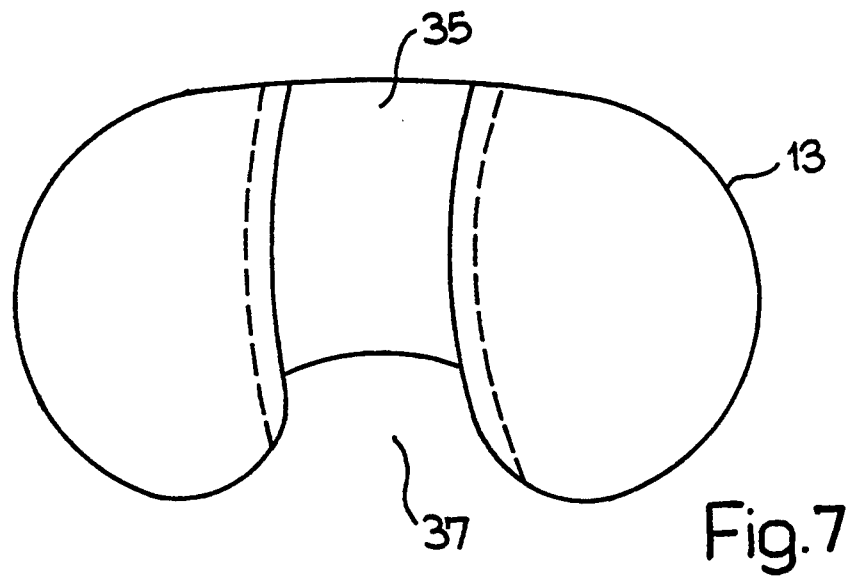
FIG. 7 is a bottom view of the meniscal part of the joint of FIG. 5.
Figure 6:
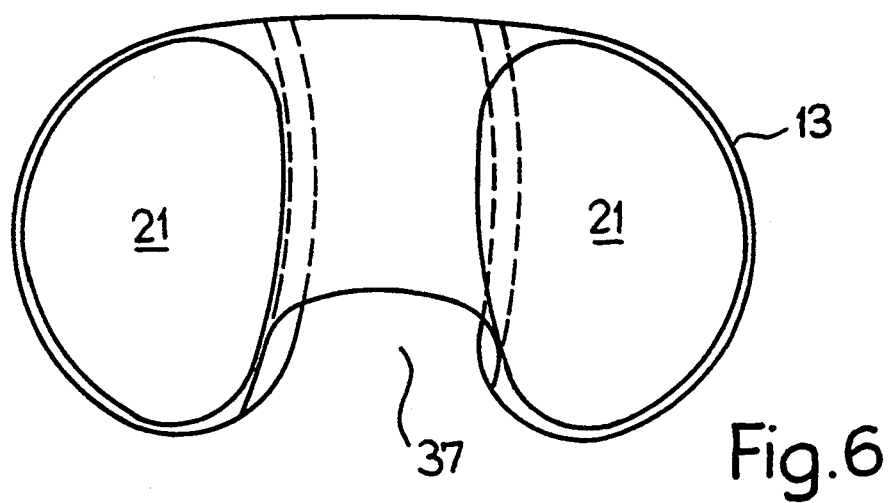
FIG. 6 is a top view of a, first intermediate or meniscal part of the joint.
Figure 8:
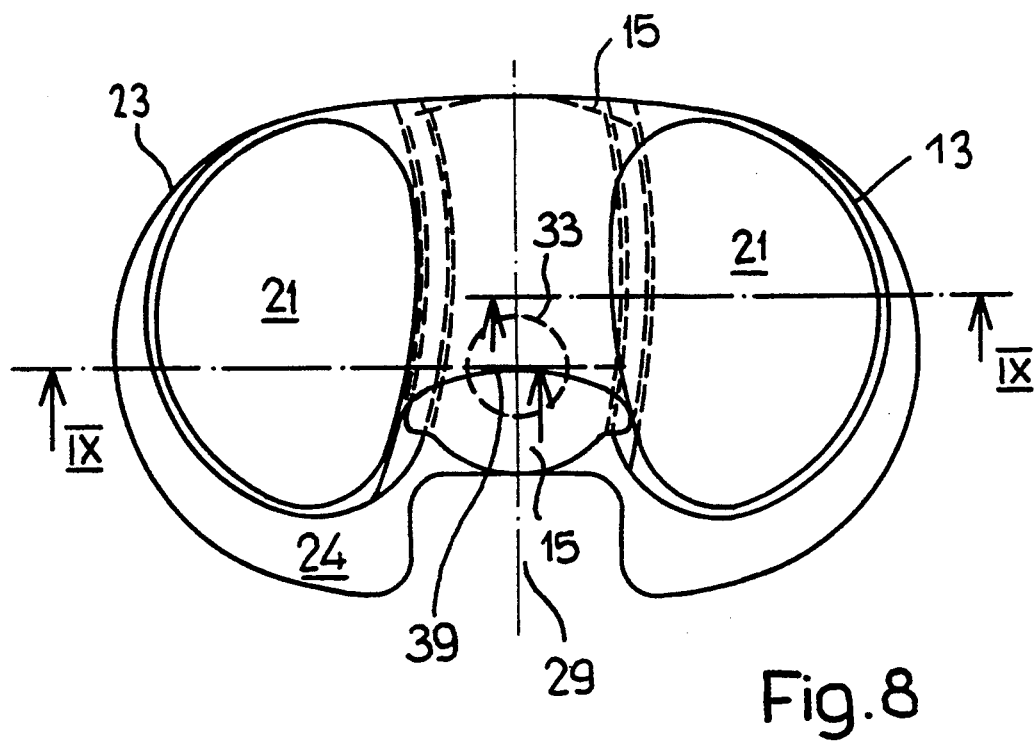
FIG. 8 is a top view of the second prosthetic or tibial part, with the coupling part and the meniscal part inserted.
Figure 10:
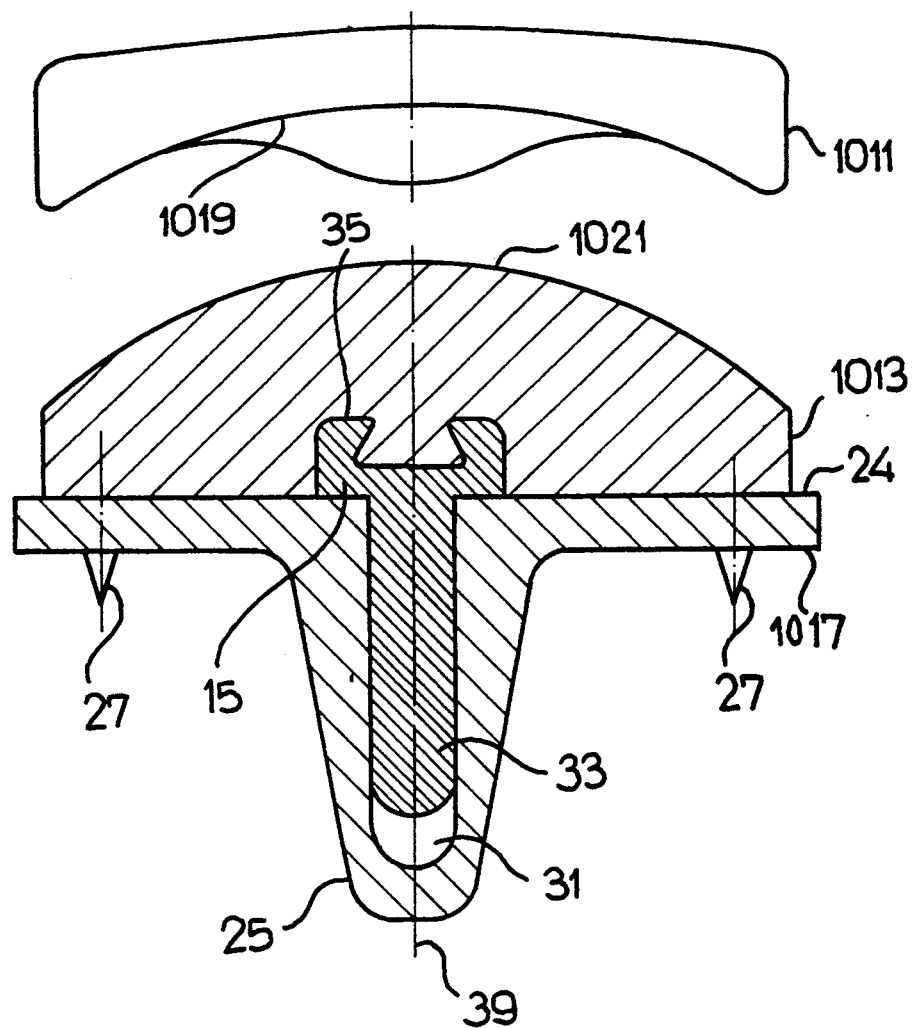
FIG. 10 is a cross section through another embodiment of the knee prosthesis.
Figure 11:
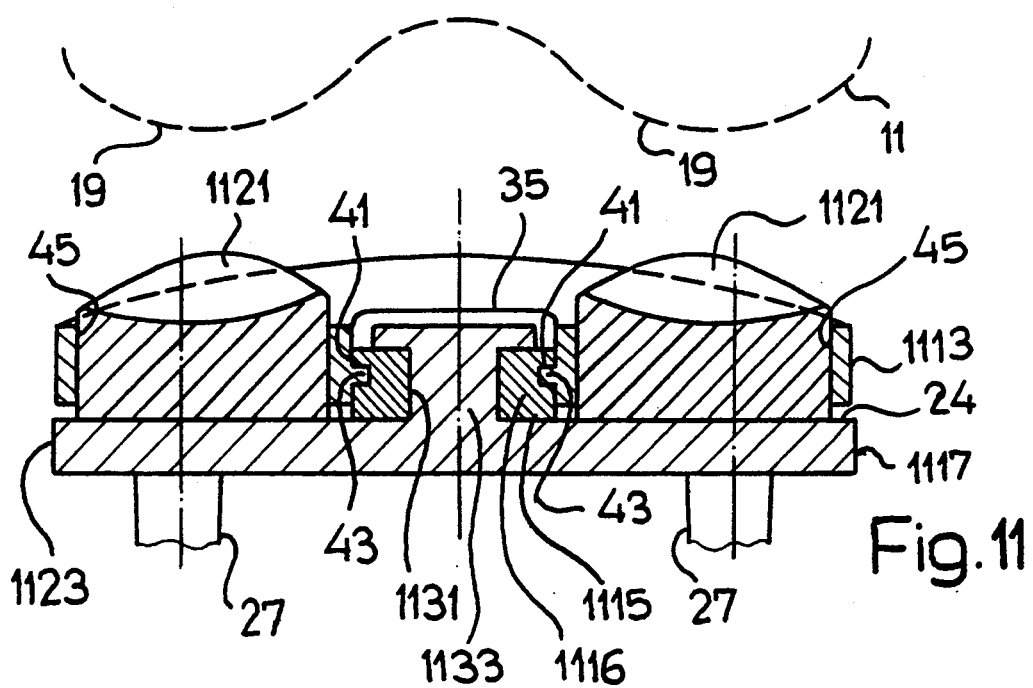
FIG. 11 is a cross-sectional view through another embodiment of a knee joint prosthesis.

The first prosthesis part 11 is preferably supplied with an attachment, or anchoring element, as well known, and not shown in FIG. 5. It has at least one rotary joint portion. It is of importance, of course, that the rotary joint portion of the first prosthesis part 11 fits together with the first intermediate or meniscal part 13. As shown in FIG. 5, the first prosthesis part 11 includes two projections or condyles 19. These condyles 19 fit on corresponding matching bearing surfaces 21 of the first intermediate part 13. The second prosthesis part 17 has a plate 23 on which a slide surface 24 is located. Conical attachment posts 27 extend downwardly from plate 23. An additional hollow attachment post 25 likewise extends downwardly. As best seen in FIGS. 8 and 9b, plate 23 has a generally oval shape, matching the outline of the natural tibial condyles, and including a posterior recess 29 for the posterior cruciate ligament. The central anchoring post or portion 25 is relatively large. In accordance with a feature of the invention, the post 25 is hollow and formed with a bore 31 to receive the rotation pin 33 of the coupling part 15. The first intermediate or meniscal part 13 is formed with a guide track 35, shaped to define a dovetail or interengaging guide track with respect to a guide portion 16 of the coupling part 15. Other suitable cross sections may be used, as illustrated in FIGS. 10, 11 and 12. Guide track 35 is positioned essentially centrally in the first intermediate part 13 and extends approximately sagittally in a curved path which is curved in a medial direction, and as best seen in FIG. 7.

FIGS. 8 and 9a illustrate the first intermediate part 13, superimposed on plate 23. As can be seen, the first intermediate part 13 has generally similar shape as that of plate 23, but is substantially narrower in sagittal direction than plate 23. The intermediate part 13 also is formed with a recess 37 for the posterior cruciate ligament.

Use and Operation

Considering FIGS. 8, 9a and 9b. It can be clearly seen that the first intermediate part 13 can carry out a pivotal movement about the axis 39, which is the central axis of bore 31 in the central post 25 of the second prosthesis part 17, as well as translatory movement from anterior to posterior, and reverse. These movements are guided, limited and controlled by the ligaments of the knee joint after the prosthesis is installed in the knee. The general movement upon flexion and extension corresponds essentially to the physiological kinematic characteristics of the knee joint.

The first prosthesis part 11 as well as the second prosthesis part 17, and the coupling part 15 with the pivot pin 33, preferably, are made of a metal alloy, of a composition customary for joint prostheses. The first intermediate part 13 may be of metal, but preferably is made of a plastic material, also as is customary for joint prosthesis.

The example illustrates two condyles and bearing surface pairs 19, 21. It is also possible to use only a single condyle/bearing surface pair. Other movable jointed connections, for example a hinge joint coupled by a hinge pin, could be used, in combination with the first intermediate part 13 which permits both translatory as well as rotary movement. The first intermediate part 13 then will have to be constructed to fit and accept such a hinge element.

In the example illustrated, the condyles 19 of the first prosthesis part 11 are convex; the matching bearing surfaces 21 of the intermediate part 13 are concave, matching the condyles 19 in shape. This imitates a natural knee joint. It is, however, also possible, where it is e.g. suggested by nature, for example by the patellafemoral joint, to form a condyle on the first intermediate part 13 and to shape the first prosthesis part with suitable concave bearing surfaces, as-shown in FIG. 10.

Embodiment of FIG. 10

In this prosthesis there is only one condyle and one bearing surface. In other respects, however, the general arrangement is substantially the same as described in connection with FIGS. 5-9a and 9b. However, the bearing surface 1019 of the first prosthetic part 1011 is concave, and the matching bearing surface 1021 on the first intermediate part 1013 then is convex. Such a prosthesis is suitable for the patella-femoral joint. The second prosthesis part 1017 will be attached to the kneecap.

Embodiment of FIG. 11

The second prosthesis part 1117 includes a central rotation pin 1133, about which the coupling part 1115 can turn. The coupling part 1115 is formed with a bore 1131 to receive the pin 1133. The guide portion 1116 of the coupling part 1115 is formed with lateral grooves 41 to receive a rib 43 which fits into the lateral grooves 41 to engage the rib 43 which is part of the intermediate part 1113. The groove and rib can be exchanged on the relevant parts. The first intermediate part 1113 is thus held spaced from the surface 24 of the plate 1123 of the second prosthesis part 1117. The bearing surfaces 21 are formed on replaceable bearing elements 1121, fitted into recesses 45 of the first intermediate part 1113, and engaging the surface 24 of plate 1123. Groove 41 and rib 43 form a tongue and groove connection.

In use, and upon rotary and/or translatory movement, the bearing elements 1121 of the first intermediate part 1113 slide on the surface 24 of plate 1123. The bearing elements 1121, preferably, are made of plastic material suitable and customarily used in implanted prosthetic devices. The first intermediate part 1113 can be made of metal while the guide portion 1116 is made of plastic, or vice versa. Thus, it is possible to use a pairing of plastic and metal at the respective engaging surfaces.

As can be seen by a comparison of FIGS. 9a, 9b with FIG. 11, for example, the difference, in essence, is this: In the embodiment of FIGS. 9a, 9b, pivot means 33 extends downwardly from the coupling part 15 in form of a post or pin 33, which extends into the bore or holes 31 of the tibial attachment post 25. In the embodiment of FIG. 11, the pivot pin 1133 extends upwardly from the second prosthetic part 17, and is recessed in the coupling part 1115 within the bore 1131 thereof.

Figure 12B:
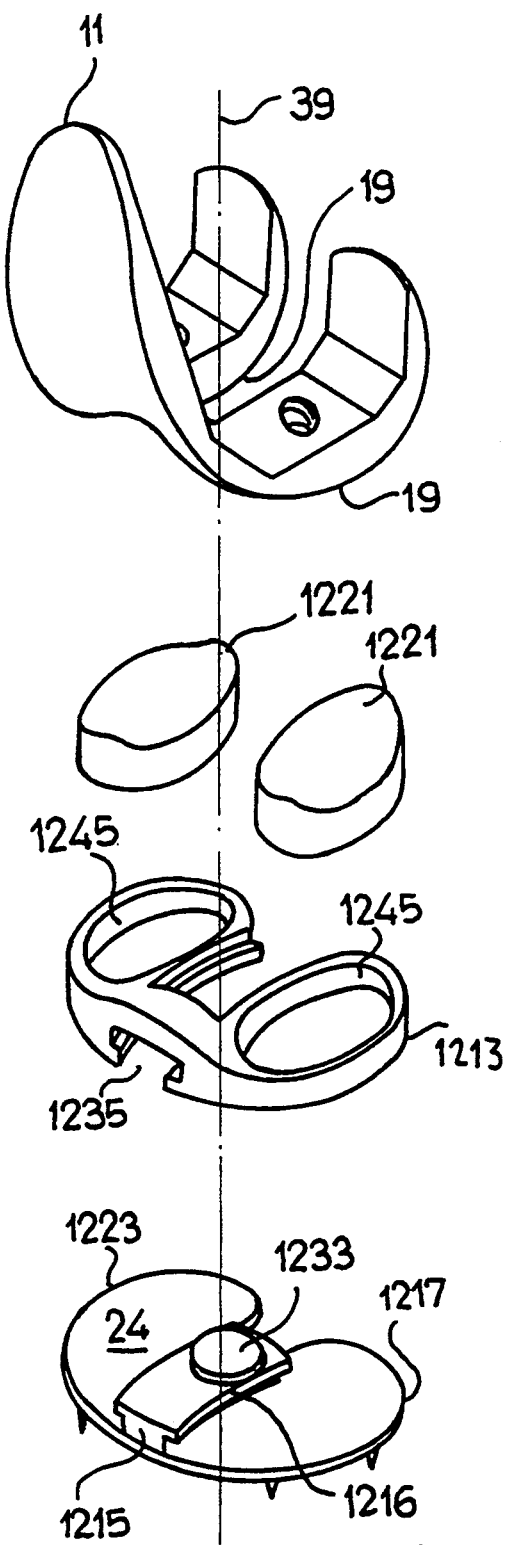
FIG. 12b illustrates the joint of FIG. 12a in exploded view.
Figure 12A:
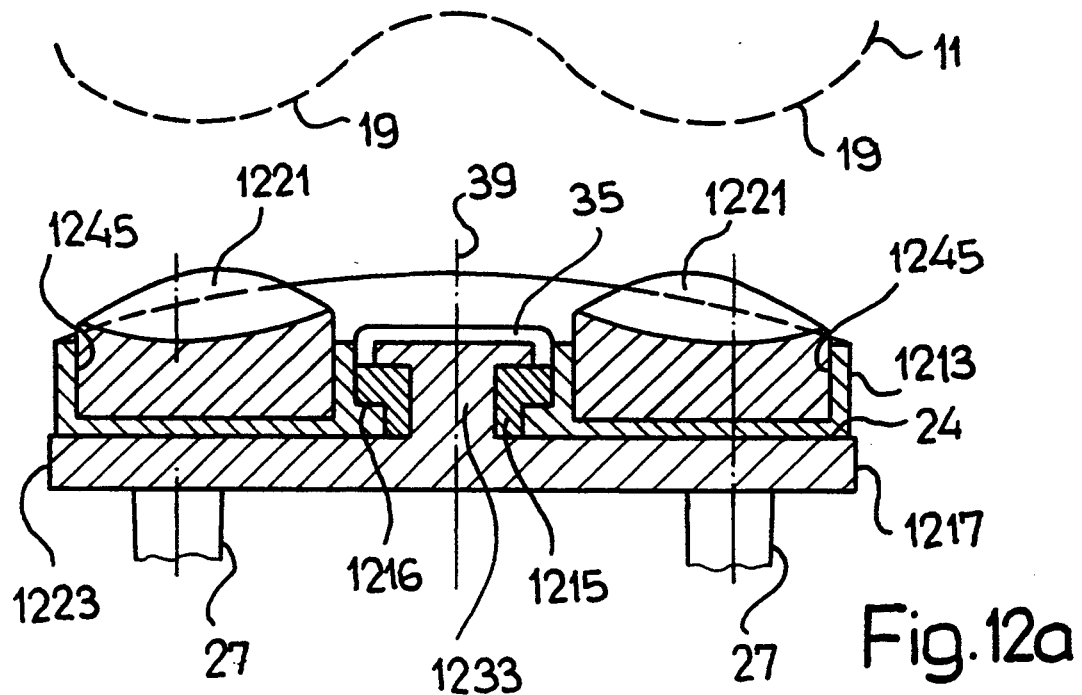
FIG. 12a is a cross section through yet another embodiment of the prosthesis.

Embodiment of FIGS. 12a and 12b

The difference between the embodiments of FIGS. 11 and 12 is the construction of the bearing elements 1221 and the intermediate part 1213. In FIG. 12, the recesses 1245 in the intermediate part 1213 do not extend down to the surface 24 of the plate 1223 of the second prosthesis part 1217. Rather, they are held in suitable pockets. The guide portion 1216 of the second intermediate part 1215 also has been given a stepped shape, held in a central pin 1233. This illustrates another retention or coupling construction.

Figure 13A:
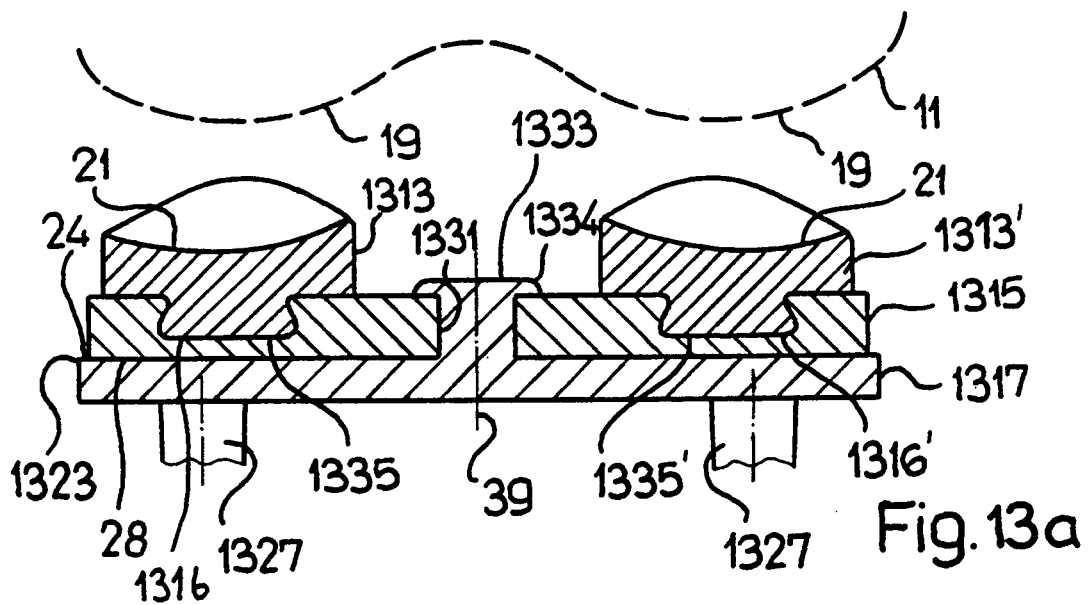
FIG. 13a is a schematic cross-sectional view along line XIII—XIII of FIG. 14 of another embodiment of the invention.
Figure 14:
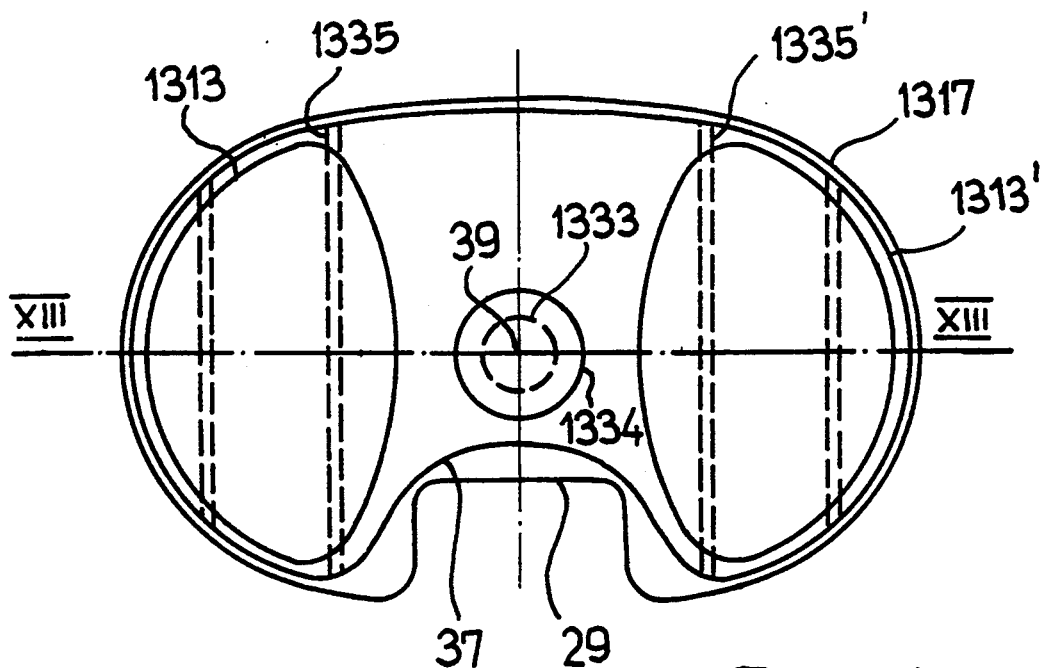
FIG. 14 is a top view of the embodiment of FIG. 13.

Embodiment of FIGS. 13a, 13b and 14

The embodiment of the prosthesis shown has two separate meniscal parts 1313, 1313', a second intermediate part 1315, a first prosthesis part 11, and a second prosthesis part 1317. The second prosthesis part 1317 has a plate 1323 with a slide surface 24 thereon. The slide surface 24 may be formed by a layer 1324 of plastic material (FIG. 13b). Conical or otherwise suitably shaped attachments posts, pins or fins 1327 extend from the plate 1317 downwardly, for attachment into the tibia. The shape of plate 1317, as best seen in FIG. 14, is similar to that of the plate 23, see FIGS. 6 and 7, formed with a recess 29.

The second prosthesis part 1317 is formed with an upwardly projecting pivot pin 1333, which fits into a bore 1331 formed in the second intermediate part 1315. The pin 1333 (FIG. 13a) may be formed at its upper end with an overlapping rim 1334, or another element, such as a screw 1334' (FIG. 13b), a snap ring or the like may be provided, to prevent dissociation and lifting off of the second intermediate part 1315 from the slide surface 24.

In accordance with a feature of the invention, the second intermediate part 1315 is formed with two guide means, e.g. grooves 1316, 1316'. The grooves, preferably, have dovetail shape or any other suitable cross section, which is shaped to prevent unintended lifting off or removal of the meniscal elements 1313, 1313'. The guide means 1316, 1316' are located in the intermediate part 1315 to extend essentially parallel to each other and are directed in essentially sagittal orientation, see FIGS. 13a and 14.

Use and operation

FIGS. 13a and 14b clearly show that the second intermediate part 1315 can readily pivot about the axis 39. The meniscal parts 1313, 1313' permit additionally translatory movement between anterior and posterior direction. These movements are guided and limited by the ligaments of the knee joint, after installation of the prosthesis. The kinematics of movement correspond generally to the physiological characteristics of movement of a knee joint.

Preferably, the first and second prosthesis parts 11, 1317 and the first intermediate part 1315 are made of a metal alloy usual, customary and suitable for joint prostheses. The meniscal parts 1313, 1313' preferably are made of a plastic, again of customary composition in knee joint replacements. Because of the congruence of the bearing surfaces 19, 21 and the condyles 19, the meniscal parts 1313, 1313' can also be made of metal. In certain cases it is advisable to have a plastic coating on one of the cooperating bearing surfaces, e.g. on the bearing surfaces 24, 28 of second prosthetic part 1317 and the second intermediate part 1315, respectively. Accordingly, it is possible to have always a pairing of plastics and metal for the different bearing surfaces, or a suitable metal or hard material pairing. Two condyle-bearing surface pairs 19, 21 are used in this embodiment. It is also possible to use only a single condyle-bearing surface pair.

Figure 15:
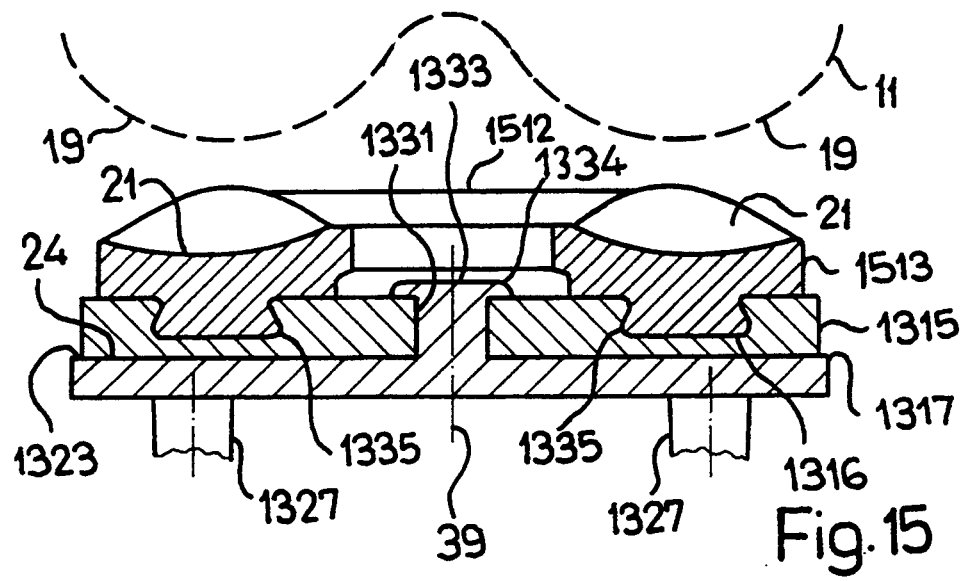
FIG. 15 is a cross-sectional view along line XV—XV of FIG. 16.
Figure 16:
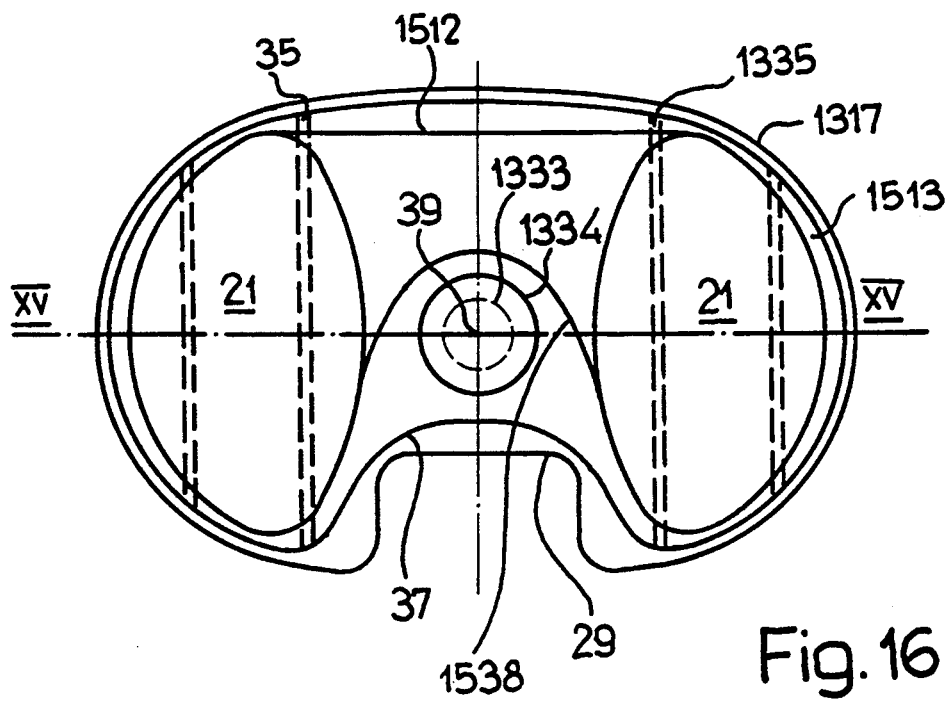
FIG. 16 is a top view of the embodiment of FIG. 15.

Embodiment of FIGS. 15 and 16

The difference between the embodiment of FIGS. 13a, 13b and 14, and of FIGS. 15 and 16 is that a common meniscal part 1513 is used for cooperation with the condyles 19 of the first prosthesis part 11. This meniscal part 1513 is formed with a recess 1538 for the posterior cruciate ligament.

Rather than considering the meniscal part 1513 as a single unit, it can also be considered as the two meniscal parts 1313, 1313' of FIGS. 13 and 14 which are coupled together by a bridge 1512 (see FIGS. 15 and 16). Preferably, however, the meniscal part 1513 of FIGS. 15 and 16 is a single, unitary structure. It is formed with two bearing surfaces 21. In all other respects, the prosthesis is similar to that described in connection with FIGS. 13a, 13b and 14.

Figure 17A:
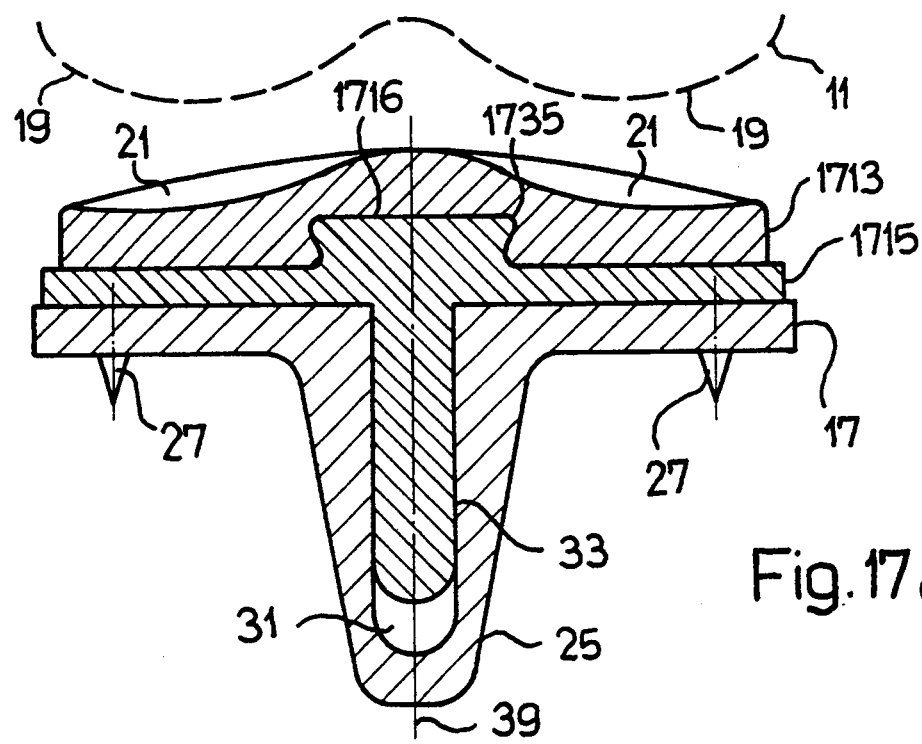
FIG. 17a is a cross-sectional view along line XVII—XVII of FIG. 18.
Figure 18:
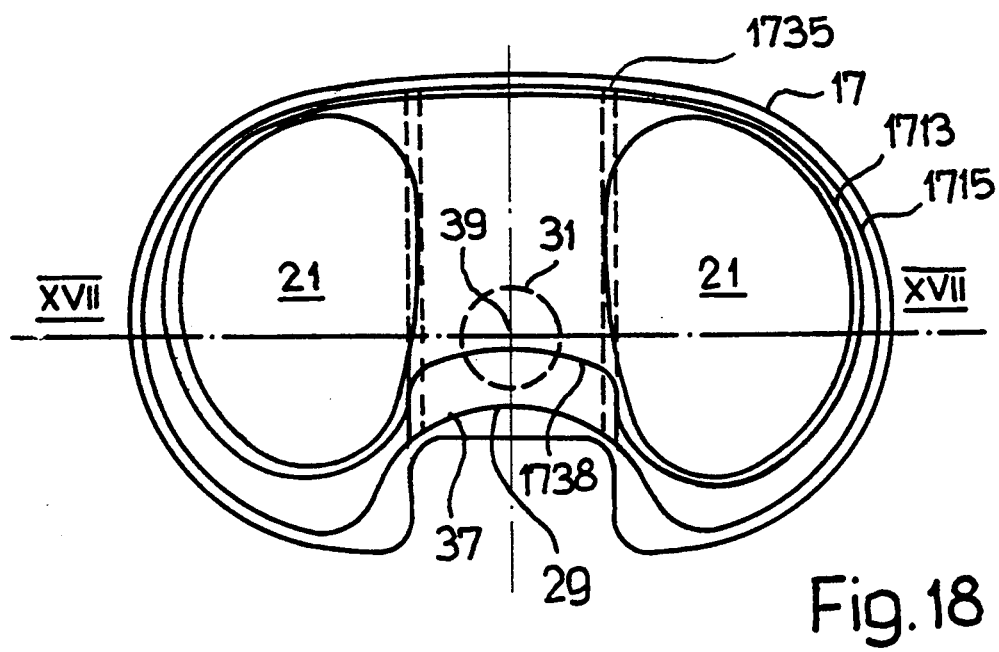

The embodiment of FIGS. 17a, 17b and 18 are similar to those described in connection with FIGS. 15 and 16. For both condyles 19, a common meniscal part 1713 is used. It is formed with the recess 1738 to receive the posterial cruciate ligament. It is further formed with two bearing surfaces 21 and centrally positioned guide track 1735 which receives the guide portion 1716 of the second intermediate part 1715. The rotation pin or post 33 extends from the second intermediate part 1715, in a post and pin reception construction similar to that shown in FIGS. 8 and 9a, 9b. Again, rotary movement about axis 39 is possible, combined with translatory movement in the guide track 1735. The common meniscal part 1713, in the dorsal direction, is formed with a recess 1738 for the dorsal or posterior cruciate ligament. The second intermediate part 1715 may have on the underside a layer 1715' of plastic material (FIG. 17b).

Figure 19A:
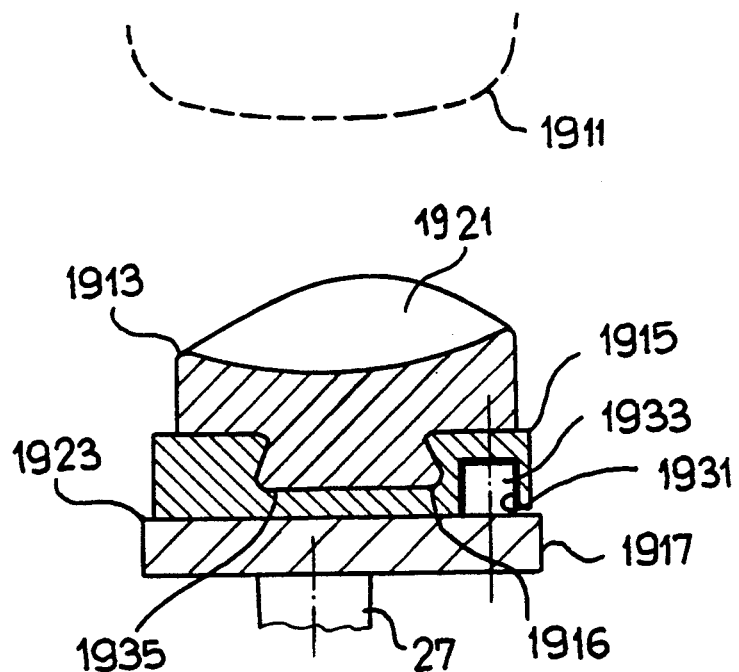
FIG. 19a is a fractional detail view of another embodiment of the prosthesis, taken along line XIX—XIX of FIG. 20.
Figure 20:
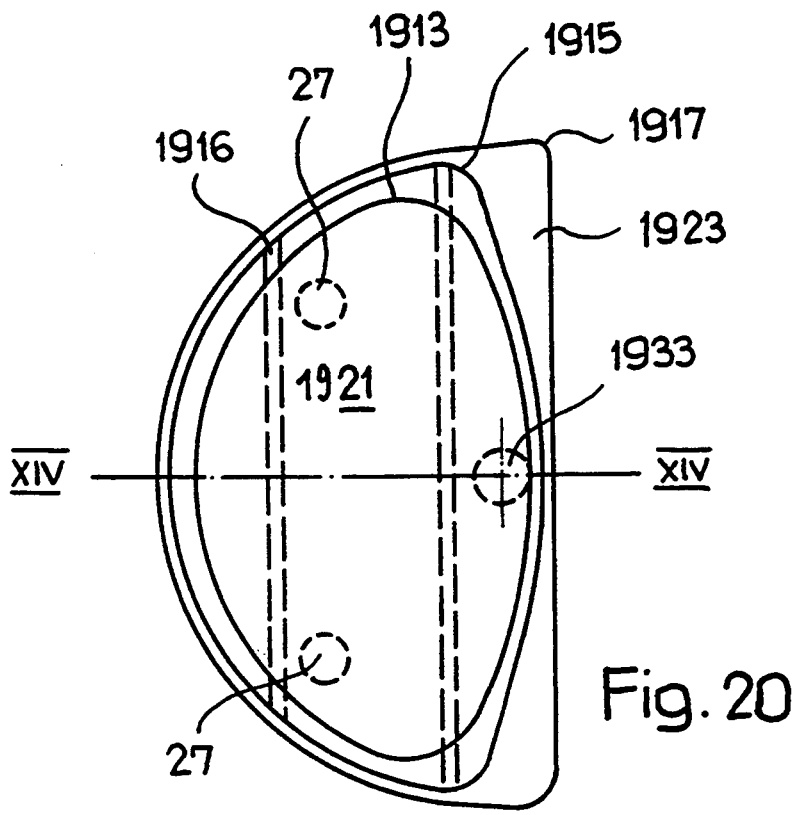
FIG. 20 is a top view of the embodiment of the prosthesis of FIG. 19.
Figure 19B:
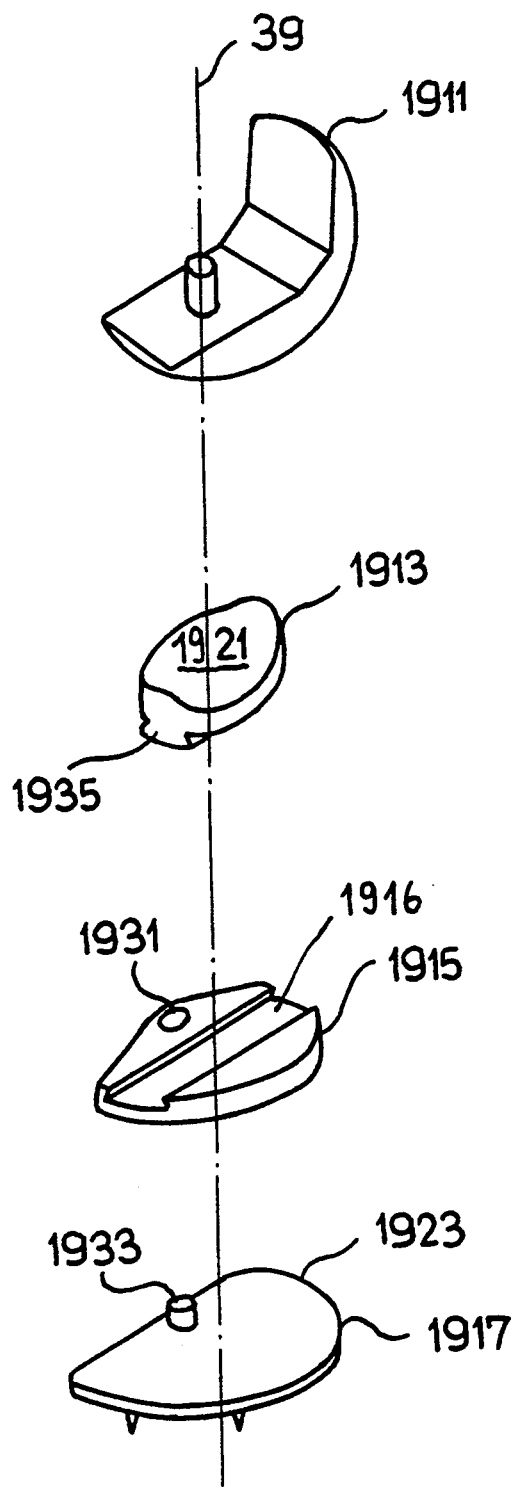
FIG. 19b illustrates the joint of FIG. 19a in exploded view.

FIGS. 19a, 19b and 20 illustrate a mono-compartmental joint prosthesis which, basically, is similar to the bi-compartmental prosthesis of FIGS. 15a, 15b and 16.

There is a first prosthetic part 1911 and a first intermediate part 1913. The second intermediate part 1915 is formed with a bore 1931 into which the rotation post 1933 from the second prosthesis part 1917 fits. The second intermediate part 1915 can rotate on the top surface of the plate 1923 around the post 1933. The second intermediate part 1915 formed with a guide track 1916, similar to the guide track 1316 (FIGS. 13a, 13b, 14). FIGS. 19a, 19b and 20 do not show any specific elements similar to the overlapping cap 1334 (FIGS. 13a–16) which prevents dislocation of the intermediate part 1933. Any suitable arrangement to prevent such unintended vertical dislocation can be used, for example a groove in the post 1933 into which an internal circumferential rib or internal projections fit, use of a C snap ring or the like. Such elements have been omitted from the drawing for simplicity. Guide portion 1935 corresponds to guide portion 1735, FIGS. 13a, 13b. Condyle 1919 fits against surface 1921.

Embodiment of FIG. 21

The femoral part 2111 is a dual-element part. FIG. 21 illustrates the arrangement of the respective parts of the knee joint in exploded view, and shows the femoral part 2111, the meniscal part 2113, the coupling part 2115 and the tibial part 2117 with a fastening post 2125 for attachment to the tibia of the user. The femoral part 2111 has a base portion 2112 and a stabilizing portion 2114, which can be separately fitted on and secured to the base portion 2112. The femoral part 2111, which is thus formed, has an attachment post or attachment section 2156 for attachment of the part 2111 in the femur. Remote from the femoral attachment is a rotary joint section or portion which has two spherically curved surfaces 2119, forming condylar surfaces. As best seen in FIG. 22, the surfaces 2119 which are convex and, for example, spherical, have a general radius R. This deviates slightly from the more elliptical shape of the natural knee which is represented by the broken line 2151. The spherical surfaces 2119 fit into concave bearing surfaces 2121, which also have the radius R, in order to ensure congruence, which substantially reduces wear and tear on the materials of the joint.

The tibial part 2117 has a plate 2123 with a slide surface 24 thereon. A conical anchoring post 2125 extends from plate 2123. The plate 2123 is shaped to match the usually oval form of a natural tibia socket for the femoral condyles. It is formed with a posterior recess 29 for the posterior cruciate ligament. The attachment post 2125 is relatively large and is formed with an opening 31 to receive a pin 33 of the coupling part 2115.

The meniscal part 2113 is formed with a guide track 2135, in dovetail shape, into which the guide portion 2116 of the coupling part 2115 fits. This portion of the knee structure of FIG. 21 is essentially similar to that described in connection with FIGS. 8 and 9. Other interlocking or interengaging arrangements for the guide groove or track 2135 and the guide portion 2116 of the coupling part 2115 can be used, as described in connection with FIGS. 8 and 9. The guide track 2135 may be straight or, preferably, can be formed in a medially bent path. A straight track has the advantage that the meniscal element 2113 can be used for either the right or left knee joint, and a possible mistake due to interchange of elements is excluded.

The meniscal part 2113 is similarly shaped to the shape of the plate 2123. In sagittal direction, it is narrower than the plate 2123. The meniscal part 2113 also is formed with a recess 37 for the posterior cruciate ligament. The guide portion 2116 of the coupling part 2115 fits into the guide track 1935 of the intermediate or meniscal part 2113. The pin 33 extends downwardly.

In accordance with a feature of the present invention, the coupling part 2115 is formed with a stabilization extension 2136 extending in a direction opposite to that of the pin 33, that is, in FIG. 21 upwardly. FIG. 21 also shows the axis of rotation of the guide element 2115, shown by chain-dotted line 39.

Figures 23, 24:
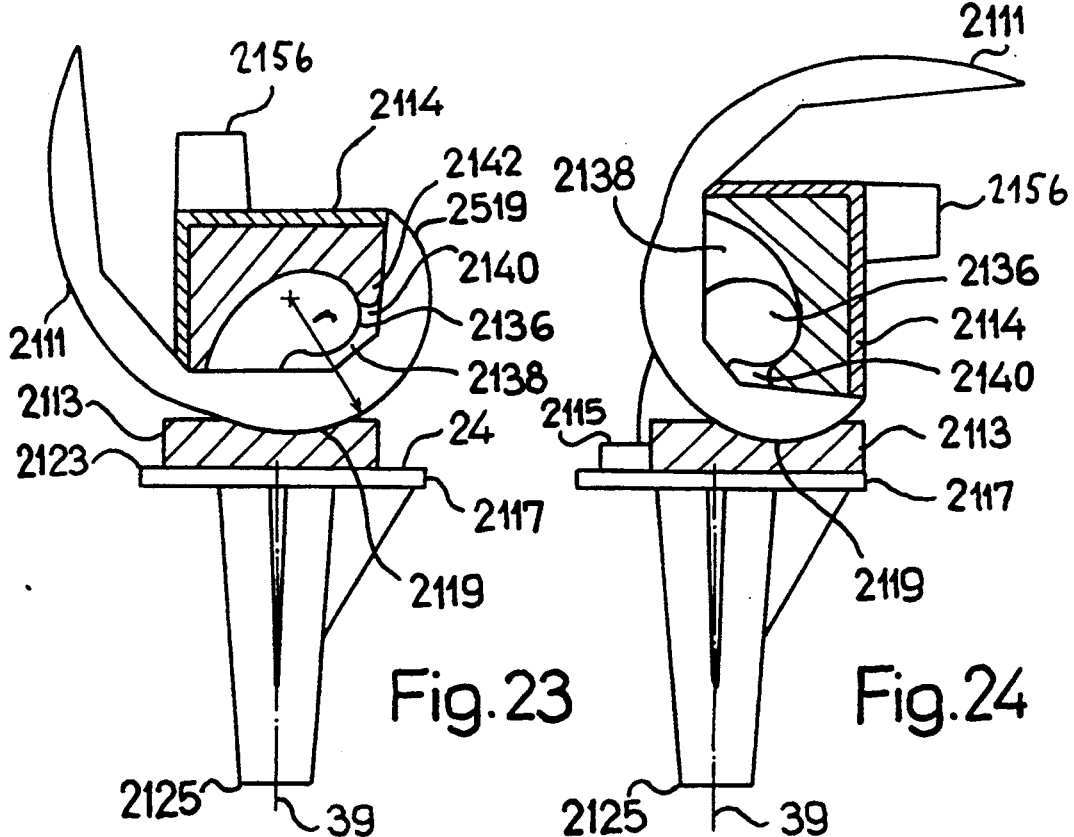
FIG. 23 illustrates the prosthesis of FIG. 21 upon extension.
FIG. 24 illustrates the prosthesis of FIG. 21 in 90° flexion.

FIGS. 23 and 24 clearly show how the stabilizing extension 2136 of the coupling part 2115 cooperates with the stabilizing portion 2114 of the femoral part 2111. This cooperation is particularly desirable if the ligamentary structure is missing or impaired, for example weak, while ensuring stability to the knee joint.

In accordance with a feature of the invention, the stabilizing projection 2136 is so made that it fits inside the interior of the box-like structure 2114, which is hollow. This box-like structure 2114 has lateral side walls 2140 which guide the stabilizing projection 2136 within the interior space 2138. This prevents medial or lateral misalignment of the axes, and, therefore, prevents a knock-knee or bowlegged position of the legs due to lateral weaknesses in the knee. The downwardly inclined projecting nose 2142 (FIG. 23) ensures stability in posterior direction, that is, motion of the tibial part 2117 is limited in posterior direction.

The femoral part 2111, the tibial part 2117 and the second intermediate or coupling part 2115 preferably all are made of a metal alloy, of the type customary and usual for joint prostheses; the meniscal or first intermediate part 2113 may be made of plastic material, as usual for joint prostheses. As mentioned earlier, it may, however, be made of a metal alloy since, because due to the described congruent construction of the rotary joint portions 2119 on the concave surfaces 21, the area or surface pressure, and thus the frictional wear, can be held to a minumum. It is also possible to use ceramic materials for all parts. Metal alloys, however, are preferred since they are more ductile than ceramics.

Considering FIGS. 21, 23 and 24, it can be seen that the first intermediate part 2113 permits translatory movement between anterior and posterior direction upon flexion as well as pivoting movement about the axis 39. The general kinematics of movement are similar to that of a natural knee.

Figures 25, 26, 27:
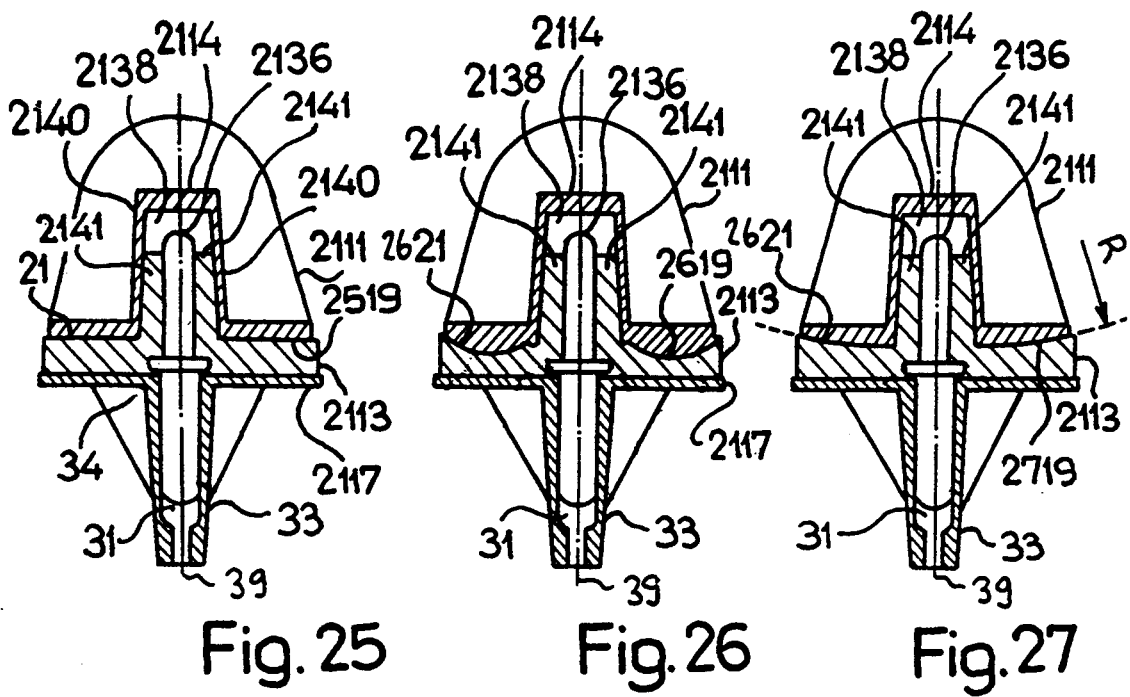
FIG. 25 illustrates, in fragmentary cross section, a cylindrical formation of the rotary joint portion.
FIG. 26 illustrates a ,spherical shape of the condyles of the rotary joint portion.
FIG. 27 illustrates a spherical shape of the rotary joint portion.

FIGS. 25–27 illustrate variations within this embodiment. The lateral walls 2141 extend from the meniscal part 2113 into the interior 2138 of the box-like stabilizing structure 2114, and prevent direct contact of the stabilizing element 2136 with the side walls 2140. FIG. 25 illustrates an arrangement in which the rotary joint portion 2519 is cylindrically curved with radius r, as indicated in FIG. 23. FIG. 26 illustrates the situation in which two condylar spherically curved surfaces 2619 are provided, fitting on matching surfaces 2621. The condylar curved regions 2719, FIG. 27, in contrast; are curved with a radius R, which is a common radius for both condylar projections 2719', and which are almost conical because the radius R is so much larger than the radius r. Surface 2721 also has radius R.

FIGS. 28a, 28b and 28c illustrate examples of a complete set of replacement knee elements for various situations. The set of FIG. 28a is suitable for a case in which the posterior cruciate ligament as well as the lateral ligaments are in good condition and are maintained and retained; FIG. 28b shows a prosthesis in which the posterior cruciate ligament is missing, and only the lateral ligaments are retained; and FIG. 28c a prosthesis in which neither the posterior cruciate ligaments nor the lateral ligaments are retained.

All three knee joint prostheses utilize the same meniscal part 2813 which, therefore, is shown only in FIG. 28a. All three sets use the same tibial part 2817 which, likewise, is shown only once. In the shown two-element construction of the femoral part of FIGS. 28b, 28c, the same base unit 2812, shown integrally only in FIG. 28a, is used. The stabilizing elements, however, are different and the stabilizing elements 2814 (FIG. 28b) or 2814' (FIG. 28c) are fitted to the base part 2812, which, for example, is slipped over the part 2814 and locked thereto. The condylar surface 2819 can be in accordance with any suitable shape, described elsewhere.

The second intermediate or coupling part 2815 can be different for the three respective different cases. In the coupling part 2815 of FIG. 28a, the stabilizing portion is not needed; in FIG. 28b, the coupling part 2815' has a projection 2836' which is provided merely for stabilizing in posterior direction The coupling part 2815" of FIG. 28c, has a projecting portion 2836" which ensures stability in posterior as well as medial and lateral directions, see also FIG. 21.

FIG. 29a shows single or unitary femoral parts 2911, 2911' and 2911" which have base portions 2912, 2912' 2912" respectively; in the embodiments of FIGS. 29b and 29c, the box-like reception structure for the extension of the respective stabilizing elements 2815' and 2815" are integral with the base structure, as seen at 2914' (FIG. 29b) and 2914" (FIG. 29c). The entire box-like structure 29" may be formed with an additional attachment post 2916, as seen in FIG. 29c.

The embodiment of FIG. 30 is similar to that described in connection with FIG. 17b. However, the guide portion 3016 is located on the second prosthetic part 3017 and the guide track 3035 on the second intermediate part 3015. Further, the rotation post 3033 is facing upward from the second intermediate part 3015 to engage the bore 3031 of the first intermediate part 3013.

Various changes and modifications may be made. Any features described in connection with any one the embodiments, may be used with any other embodiments, within the scope of the inventive concept; for example, the shape of the guide tracks can be varied, and the differently shaped guide tracks, FIGS. 10, 11, 12 as well as combined or independent meniscal units with the bearing surfaces 21 can be used in any one of the embodiments, with or without a stabilizing projection of the coupling part, as described in connection with FIG. 21. The vertical position of the sliding portion and the rotary portion of the joint can be reversed. Thus, the guide track 35/guide projection 15 combination can also be located on the second prosthetic part 17 and the next adjacent element of the intermediate joint means combination, i.e. the coupling part, with the pin 33/pin hole 31 combination then coupling the meniscal part and the coupling part.

I claim:

1. A prosthetic joint for replacement of a natural joint, having
    a first prosthetic part (11) including
        a bone attachment portion (2156), and
        a condylar portion (19, 2119, 2519, 2619, 2719, 2819);
    a second prosthetic part (17, 1917, 2117, 2817) including
        a bone attachment means (25, 27, 1327, 2125),
        an essentially planar sliding surface (23, 24), and
        first pivotal means (31, 1133, 1233, 1933) defining an axis of rotation (39);
    an intermediate part (13, 13a, 13b, 1113, 1913, 2113, 2813) located between said first and second prosthetic parts, said intermediate part including
        a bearing surface (21) on one side thereof for cooperation with said condylar portion;
    a second pivotal means (33, 1131, 1231, 1331) for cooperation with said first pivotal means, said first and second pivotal means forming a rotary joint and rotationally connecting the intermediate part with said second prosthetic part;
    first guide means (35, 1935) located on the intermediate part on a side thereof opposite to said one side having the bearing surface 21);
    second guide means (16, 1916) arranged for cooperation with said first guide means,
    one of said first and second guide means extending in a substantially anterior-posterior direction; and
    coupling means (15–35, 41–43, 1916–1935, 2116–2135) coupling the intermediate part and the second prosthetic part, including said second guide means.

2. The joint of claim 1, wherein said coupling means is rotatable and comprises a rotation post (33) on said second guide means (16, 1716), said post forming part of said second pivotal means; and
    reception means (25, 31) formed in said second prosthetic part (17, 1717) for pivotably supporting said second guide means for rotation about said axis of rotation (39), and forming part of said first pivotal means.

3. The joint of claim 2, wherein said bone attachment means (25) is formed as a projecting post (25) extending from a bone engaging surface of said second prosthetic part, said post being formed with a bore (31), said bore forming the first pivotal means; and
    wherein the second pivotal means comprises a pin (33) fitting in said bore (31) and attached to said coupling means.

4. The joint of claim 1, including a pin element (33') located on the second prosthetic part (17), and forming one of said pivotal means; and
    a reception bore (31, 31a, 31b) receiving said pin element, forming the other of said pivotal means, said reception bore being formed in one part of the parts consisting of at least one of said second prosthetic part, said intermediate part and said coupling means.

5. The joint of claim 1, wherein the coupling means (15) is slidable on the essentially planar slide surface (23, 24) of the second prosthetic part (17).

6. The joint of claim 1, wherein said coupling means and said guide means form a combined coupling-and-guiding system which comprises positive interengaging means including at least one connection, wherein said connection consists of at least one of the connections comprising a dovetail connection, a tongue-and-groove connection, an overlap connection, an undercut connection, and a polygonal or curved holding shell.

7. The joint of claim 1, wherein one of said guide means comprises a single guide track (35) located essentially centrally in the first intermediate part means (13).

8. The joint of claim 1, wherein the condylar portion of the first prosthetic part comprises two condyles (19);
and wherein the bearing surface on the intermediate part (13) comprises two bearing surface regions (21) shaped to receive said condyles of the first prosthetic part.

9. The joint of claim 1, wherein the condylar portion of the first prosthetic part comprises a single condyle; and
wherein the bearing surface of the intermediate part (13) comprises a single rotary surface shaped and dimensioned to be essentially congruent with said single condyle.

10. The joint of claim 1, wherein the condylar portion of the first prosthetic part comprises at least one condyle of convex shape; and
wherein the bearing surface of the intermediate part comprises a concave surface matching the configuration of the at least one condyle of the first prosthetic part.

11. The joint of claim 1, wherein said intermediate part comprises a multi-component structure, having a holding portion (1113) and bearing elements (1121),
said bearing elements having said bearing surface and being fitted in recesses (1145, 1245) of said holding portion, said holding portion retaining said bearing elements.

12. The joint of claim 11, wherein said recesses are through-bores, and said rotary joint elements are in engagement with said planar slide surface (24).

13. The joint of claim 11, wherein said recesses (1243) are in the form of blind bores, closed off by a bottom wall of the holding portion, said holding portion being in engagement with said essentially planar slide surface (24).

14. The joint of claim 1, wherein the second prosthetic part and said intermediate part are formed, respectively, with recesses (37, 29) for placement of ligaments of the natural joint therein.

15. The joint of claim 1, wherein the intermediate part (1113, 1213) includes two meniscal parts (1121, 1221) and a connecting element (1113, 1213) coupling said meniscal parts together;
the coupling means (1115, 1215) and the first guide means 935) on the intermediate part (1113, 1213) being shaped and positioned to space at least a portion of the intermediate part from said essentially planar slide surface (24); and
wherein the coupling means is rotatable on said planar slide surface.

16. The joint of claim 1, wherein said intermediate part is a two-unit structure comprising two meniscal parts (1313, 1313') and a connecting element (1315) connecting said meniscal parts together, said meniscal parts having said bearing surfaces of said connecting element, said connecting element further forming part of the coupling means; and wherein
said first and second guide means are formed on said meniscal parts and the coupling element, respecting, and include two guide track sections (1316), each of said meniscal parts being guided in one of said guide track sections.

17. The joint of claim 16, wherein the condylar portion of said first prosthetic part comprises two condyles; and
wherein each of said meniscal parts (1313, 1313') are positioned and shaped for receiving a respective one of said condyles.

18. The joint of claim 1, wherein the condylar portion of said first prosthetic part includes two condyles (19);
and wherein said meniscal parts (1513, 1713) comprise a single structural element having said bearing surface (21).

19. The joint of claim 16, wherein said first and second means comprise two spaced guide tracks (1535).

20. The joint of claim 1, wherein said condylar portion (19) on the first prosthetic part comprises a single condyle (1919); and
wherein said intermediate part comprises a single surface region (1921) for reception and fitting against said single condyle.

21. A prosthetic joint for replacement of a natural joint, having
a first prosthetic part (11) including
a bone attachment portion (2156), and
a condylar portion;
a second prosthetic part (2117, 2817) including
a bone attachment means (2125),
an essentially planar sliding surface (23, 24), and
first pivotal means defining an axis of rotation (39);
an intermediate part (2113, 2813) located between said first and second prosthetic parts, said intermediate part including
a bearing surface (21) on one side thereof for cooperation with said condylar portion;
a second pivotal means for cooperation with said first pivotal means, said first and second pivotal means forming a rotary joint and rotationally connecting the intermediate part with one of said prosthetic parts (11; 17, 1317, 1917, 2117, 2817);
first guide means (35, 1335, 1735, 1935) located on the intermediate part on a side thereof opposite to said one side having the bearing surface (21);
second guide means (15) arranged for cooperation with said first guide means,
one of said guide means extending in substantially anterior-posterior direction;
coupling means coupling the intermediate part means and the second prosthetic part, including said second guide means;
wherein the coupling means additionally includes a stabilizing portion; and
wherein said first prosthetic part (2111) includes a stabilizing section (2114) in operative association with the stabilizing portion (2136) of said coupling means (2115), said stabilizing portion and stabilizing section, respectively, having engageable surfaces to provide for stabilization of the prosthetic joint in the event that natural ligaments are weak or missing.

22. The joint of claim 21, wherein said second pivotal means comprises a rotation pin (33) formed on said coupling means; and
wherein the first pivotal means comprises a reception means (25, 31), formed on said second prosthetic part (17), and pivotably supporting said coupling means for rotation about said axis of rotation (39).

23. The joint of claim 1, wherein the bearing surface (21) and said first condylar portion, respectively, include part-cylindrically curved surface regions (2519, 2521).

24. The joint of claim 1, wherein the bearing surface (21) and said first condylar portion, respectively, include part-spherically curved surface regions (2619, 2621).

25. The joint of claim 1, wherein the condylar portion (2719) comprises a condylar element;
and wherein the first and second pivotal means comprise respective spherical surfaces (2719, 2721) which extend, with uniform curvature, over both the condylar element of the condylar portion of the first prosthetic part and the intermediate means (2113).

26. The joint of claim 1, wherein the first prosthetic part, including the bone attachment portion and said first pivotal means, comprises a single unitary structural element.

27. The joint of claim 1, wherein the joint is a knee joint and said axis of rotation extends substantially in the same direction as the axis of the tibia of the user.

28. The joint of claim 21, wherein said stabilizing section (2114, 2814, 2814', 2914', 2914") comprises a hollow box-shaped structure having interior surfaces and said stabilizing portion comprises a stabilizing element (2136) which fits therein with slight clearance between the interior of said box-shaped structure and said stabilizing element,
said stabilizing element including a projecting hook-like region having lateral surfaces fitting within said box-shaped structure.

29. The joint of claim 28, wherein said box-shaped structure has side walls; and
said intermediate part (2113) comprises lateral projections (2141) which separate the side walls (2140) of said box-shaped structure and said stabilizing element (2136).

30. A set of prosthetic joints as claimed in claim 21 for replacement of a natural knee joint in which, selectively,
(a) the posterior cruciate ligament as well as the lateral ligaments are retained;
(b) only the lateral ligaments are retained;
(c) neither the posterior cruciate ligament nor the lateral ligaments are retained,
said set including
at least two first prosthetic parts (2812) shaped for attachment to a femur;
at least two of said coupling parts (2815, 2815', 2815"),
and forming said coupling means,
at least one of said second prosthetic parts (2817) and
at least one intermediate part (2813).

31. The set of claim 30, wherein the femoral parts (2812) are single unitary elements.

32. The set of claim 30, wherein the femoral parts, each comprise a base portion (2812) and said stabilization section (2814) as a separate element fitted on said base section.

33. The set of claim 30, wherein at least one (2815', 2815") of said guide elements (2815, 2815', 2815") comprises said stabilizing portion (2836', 2836").

34. The set of claim 30, wherein the set comprises
a plurality of femoral parts (2812) of different sizes;
a plurality of intermediate (2813) of different sizes; and
a plurality of second prosthetic parts (2817) of different sizes.

35. The joint of claim 27, wherein said first prosthetic part (2911') is a multi-part element comprising a femoral section (2812, 2912) defining a base section and, as a separate and attachment element, said stabilizing portion (2136, 2814, 2814', 2914', 2914").

36. The joint of claim 22, wherein said reception means comprise a portion of said bone attachment means, said portion being in form of a projecting post (25) formed with a bore (31), and said pin (33) fitting in said bore.

37. The joint of claim 21, wherein the joint is a knee joint and said axis of rotation extends substantially in the same direction as the axis of the tibia of the user.

38. The joint of claim 1, wherein said one of said guide means is curved with a medial radius of curvature.

39. The joint of claim 21, wherein said engageable surfaces of said stabilizing section (2114) and said stabilizing portion (2136) of said coupling means include interengaging surfaces.

40. The joint of claim 21, wherein said stabilizing section (2114, 2814, 2814', 2914, 2914") and said stabilizing portion (2136) comprise, respectively, a structure defining a first surface, and a stabilizing element engageable with said first surface.

41. A prosthetic joint for replacement of a natural patella-femoral joint, having
a first prosthetic part (1011) including
a bone attachment portion, and
a condylar portion (1019);
a second prosthetic part (1017) including
a bone attachment means (25),
an essentially planar sliding surface (24), and
first pivotal means (31) defining an axis of rotation (39);
an intermediate part (1013) located between said first and second prosthetic parts, said intermediate part including
a bearing surface (1021) on one side thereof for cooperation with said condylar portion (1019);
a second pivotal means (33) for cooperation with said first pivotal means, said first and second pivotal means forming a rotary joint and rotationally connecting the intermediate part (1013) on a side thereof opposite to said one side having the bearing surface (21);
second guide means arranged for cooperation with said first guide means, and
coupling means (15–35) coupling the intermediate part and the second prosthetic part, including said second guide means;
wherein the condylar portion of the first prosthetic part comprises a condyle (1019) with an outer concave surface; and
wherein the intermediate part (1013) is formed with a convex surface (1021) fitting the concave surface (1019) of the condyle of the first prosthetic part.

42. The joint of claim 1, wherein said coupling means is rotatable and comprises a rotation post (1133, 1933)

on said second prosthetic part (1117, 1917), said post forming part of aid first pivotal means; and
- reception means (1131, 1931) formed in said second guide means (1116, 1916) which forms a guide element, for pivotably supporting said guide element for rotation about said axis of rotation (39, 1939), and forming part of said second pivotal means.

43. A prosthetic joint for replacement of a nature joint having
- a first prosthetic part (11) including
  - a bone attachment portion (2156), and
  - a condylar portion (19);
- a second prosthetic part (1317, 1917) including
  - a bone attachment means (25, 27, 1327),
  - an essentially planar surface (1323), and
  - first pivotal means (1333, 1933) defining an axis of rotation (39);
- a second pivotal means (1331, 1931) arranged for cooperation with said first pivotal means, said first and second pivotal means forming a rotary joint;
- an intermediate part including
  - a first intermediate part (1313), 1513, 1713, 1913) and
  - a second intermediate part (1315, 1715, 1915);
- the first (1313, 1513, 1713, 1913) intermediate part having a bearing surface (21) formed on one side thereof for cooperation with said condylar portion (19);
- an engagement surface formed on the second intermediate part for engagement on said planar surface of the second prosthetic part (1317, 1917);
- first guide means (1335, 1735, 1935) located on the first intermediate part on a side thereof opposite to said one side having the bearing surface (21);
- a second guide means (1316, 1716, 1916) arranged for cooperation with said first guide means and located on the second intermediate part (1315, 1715, 1915), and wherein
- one of said first and second guide means extend in a substantially anterior-posterior direction;
- said first and second guide means are located, respectively, on said first intermediate part and second intermediate parts at facing surfaces, and include coupling means coupling the first intermediate part and second intermediate part together; and
- wherein the rotary joint connects said second prosthetic part (1317, 1917) and said intermediate part means.

* * * * *

UNITED STATES PATENT AND TRADEMARK OFFICE
CERTIFICATE OF CORRECTION

PATENT NO. : 5,395,401
DATED : March 7, 1995
INVENTOR(S) : André BAHLER

It is certified that error appears in the above-indentified patent and that said Letters Patent is hereby corrected as shown below:

Title Page, in the paragraph entitled "OTHER PUBLICATIONS", line 2,
Replace "Manuel" with --Manual--.

Column 2, line 24, after "order" insert --to--.

Column 12, line 23, replace "14b" with --13b--.

Column 15, line 61, after "one" insert --of--.

Column 17, line 47 (Claim 13), replace "(1243)" with --(1245)--.

Column 19, line 22 (Claim 25), replace "means" with --part--.

Column 20, line 6 (Claim 34), replace "(2813)" with --parts--.

UNITED STATES PATENT AND TRADEMARK OFFICE
CERTIFICATE OF CORRECTION

PATENT NO. : 5,395,401
DATED : March 7, 1995
INVENTOR(S) : André BAHLER

It is certified that error appears in the above-indentified patent and that said Letters Patent is hereby corrected as shown below:

Column 20, line 53 (Claim 41), after "part" insert
--with one of said prosthetic parts;
    first guide means (35) located on the
intermediate part--.

Signed and Sealed this

Second Day of September, 1997

Attest:

BRUCE LEHMAN

Attesting Officer

Commissioner of Patents and Trademarks